US011491111B2

(12) United States Patent
Hassett et al.

(10) Patent No.: US 11,491,111 B2
(45) Date of Patent: Nov. 8, 2022

(54) THERMOSTABLE VACCINE COMPOSITIONS AND METHODS OF PREPARING SAME

(71) Applicant: The Regents of the University of Colorado, a body corporate, Denver, CO (US)

(72) Inventors: Kimberly Hassett, Medford, MA (US); Pradyot Nandi, Denver, CO (US); John Carpenter, Littleton, CO (US); Theodore Randolph, Niwot, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/448,647

(22) Filed: Jun. 21, 2019

(65) Prior Publication Data

US 2019/0380968 A1 Dec. 19, 2019

Related U.S. Application Data

(63) Continuation of application No. 15/694,023, filed on Sep. 1, 2017, which is a continuation of application No. 13/474,661, filed on May 17, 2012, now abandoned.

(60) Provisional application No. 61/487,206, filed on May 17, 2011.

(51) Int. Cl.

| | |
|---|---|
| *A61K 39/395* | (2006.01) |
| *A61K 9/19* | (2006.01) |
| *A61K 39/39* | (2006.01) |
| *A61K 39/00* | (2006.01) |
| *A61K 47/26* | (2006.01) |

(52) U.S. Cl.

CPC ................ *A61K 9/19* (2013.01); *A61K 39/00* (2013.01); *A61K 39/39* (2013.01); *A61K 47/26* (2013.01); *A61K 2039/55505* (2013.01); *A61K 2039/55572* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,592,872 | B1 | 7/2003 | Klimpel et al. |
| 7,037,510 | B2 | 5/2006 | Anderson et al. |
| 7,097,965 | B2 | 8/2006 | Klimpel et al. |
| 8,444,991 | B2 | 5/2013 | Randolph |
| 8,512,679 | B2 | 8/2013 | Hyde et al. |
| 8,808,710 | B2 | 8/2014 | Randolph |
| 9,731,020 | B2 | 8/2017 | Harel et al. |
| 9,744,227 | B2 | 8/2017 | Bronshtein |
| 10,532,093 | B2 | 1/2020 | Gill et al. |
| 2005/0186254 | A1 | 8/2005 | Roser et al. |
| 2009/0304799 | A1 | 12/2009 | Baker, Jr. et al. |
| 2010/0158951 | A1 | 6/2010 | Randolph et al. |

FOREIGN PATENT DOCUMENTS

| | | |
|---|---|---|
| WO | 200053215 | 9/2000 |
| WO | 2008118691 | 10/2008 |

OTHER PUBLICATIONS

Clausi et al. "Inhibition of Aggregation of Aluminum Hydroxide Adjuvant during Freezing and Drying." (2008) Journal of Pharmaceutical Sciences 97(6):2049-2061.

Hassell et al. "Stabilization of a recombinant ricin toxin A subunit vaccine through lyophilization." (2013) European Journal of Pharmaceutics and Biopharmaceutics 85:279-286.

Wolff et al. "Protection of aluminum hydroxide during lyophilisation as an adjuvant for freeze-dried vaccines." (2008) Colloids and Surfaces A: Physiochemical Engineering Aspects 330:116-126.

Clarkson et al. "Protein Denaturation in Foam." (1999) J. Colloid Interface Sci. 215(2):323-332.

Jangle et al. "Vacuum Foam Drying: An Alternative to Lyophilization for Biomolecule." (2012) Indian Journal of Pharmaceutical Sciences 74(2):91-100.

Clapp et al. "Vaccines with Aluminum-Containing Adjuvants: Optimizing Vaccine Efficacy and Thermal Stability." (2011) J. Pharm. Sci. 100(2):388-401.

*Primary Examiner* — Yunsoo Kim

(74) *Attorney, Agent, or Firm* — Polsinelli PC

(57) ABSTRACT

The present invention relates generally to the field of immunogenic compositions containing volatile salts. In certain embodiments, compositions and methods disclosed herein relate to producing and using novel combinations to create frozen immunogenic agents bound to adjuvant having improved formulations and improved consistency of distribution of adjuvant for storage and subsequent delivery to a subject in need thereof.

13 Claims, 17 Drawing Sheets

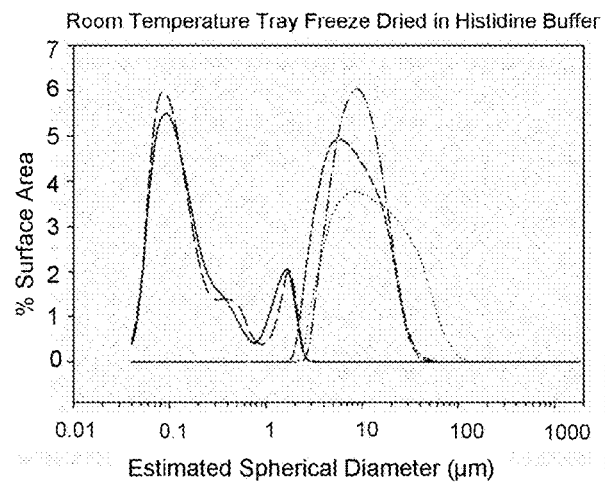
Fig. 10A
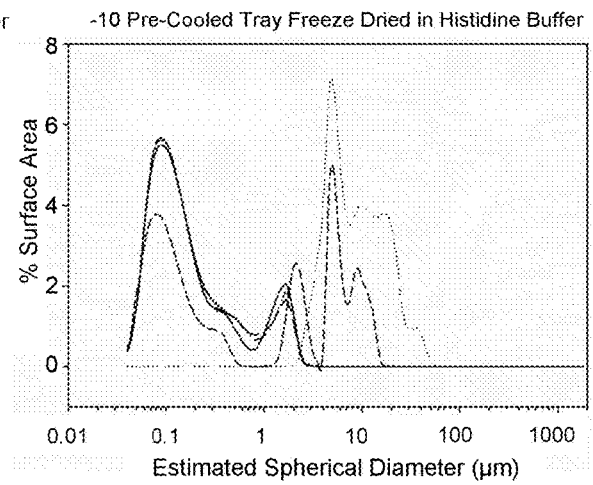
Fig. 10B
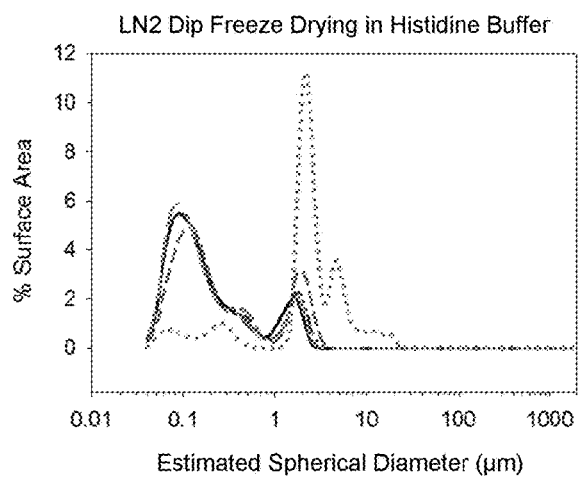
Fig. 10C
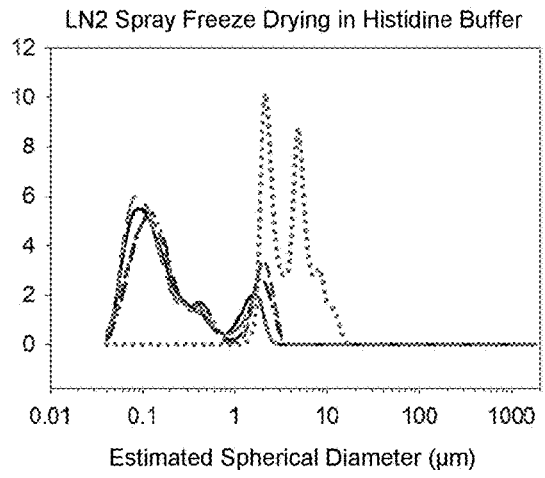
Fig. 10D
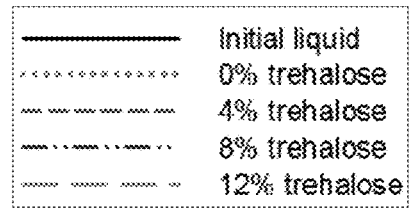

FIG. 14

| RT His + rRTA, Time 0 | | | PC His + rRTA, Time 0 | | |
|---|---|---|---|---|---|
| Mouse # | Endpoint Titers | Neutralizing IC₅₀ Titers | Mouse # | Endpoint Titers | Neutralizing IC₅₀ Titers |
| 31 | 80000 | 0 | 51 | 160000 | 25 |
| 32 | 160000 | 50 | 52 | 80000 | 500 |
| 33 | 160000 | 300 | 53 | 320000 | 600 |
| 34 | 40000 | 50 | 54 | 40000 | 25 |
| 35 | 40000 | 350 | 55 | 40000 | 0 |
| 36 | 40000 | 50 | 56 | 320000 | 400 |
| 37 | 320000 | 600 | 57 | 320000 | 50 |
| 38 | 160000 | 50 | 58 | 40000 | 50 |
| 39 | 80000 | 50 | 59 | 160000 | 100 |
| 40 | 160000 | 400 | 60 | 10000 | 0 |
| # mice with neut. capacity | 9 out of 10 | | # mice with neut. capacity | 8 out of 10 | |

| RT His + rRTA, Time month 1 | | | PC His + rRTA, Time month 1 | | |
|---|---|---|---|---|---|
| Mouse # | Endpoint Titers | Neutralizing IC₅₀ Titers | Mouse # | Endpoint Titers | Neutralizing IC₅₀ Titers |
| 111 | 16000 | 0 | 131 | 8000 | 25 |
| 112 | 32000 | 0 | 132 | 4000 | 10 |
| 113 | 64000 | 150 | 133 | 160000 | 150 |
| 114 | 64000 | 25 | 134 | 80000 | 10 |
| 115 | 128000 | 150 | 135 | 80000 | 25 |
| 116 | 32000 | 25 | 136 | 40000 | 100 |
| 117 | 500 | 0 | 137 | 160000 | 100 |
| 118 | 2000 | 0 | 138 | 80000 | 200 |
| 119 | 32000 | 10 | 139 | 80000 | 150 |
| 120 | 256000 | 600 | 140 | 40000 | 100 |
| # mice with neut. capacity | 6 out of 10 | | # mice with neut. capacity | 10 out of 10 | |

FIG. 16

| Mouse # | Liquid His + rRTA | | 
|---|---|---|
| | Endpoint Titers | Neutralizing IC$_{50}$ Titers |
| 21 | 640000 | 600 |
| 22 | 160000 | 0 |
| 23 | 80000 | 0 |
| 24 | 160000 | 250 |
| 25 | 160000 | 150 |
| 26 | 5000 | 0 |
| 27 | 160000 | 50 |
| 28 | 40000 | 50 |
| 29 | 40000 | 0 |
| 30 | 80000 | 0 |
| | # mice with neut. capacity | 5 out of 10 |

FIG. 17

THERMOSTABLE VACCINE COMPOSITIONS AND METHODS OF PREPARING SAME

RELATED APPLICATIONS

This application is a continuation of U.S. patent application Ser. No. 15/694,023, filed on Sep. 1, 2017, which is a continuation of U.S. patent application Ser. No. 13/474,661, filed on May 17, 2012, which claims the benefit of priority of U.S. Provisional Application No. 61/487,206, filed on May 17, 2011. These applications are incorporated herein by reference in their entirety for all purposes.

GOVERNMENT SUPPORT STATEMENT

This invention was made with government support under grant UO1-A1-08-2210 from the National Institutes of Health. The government has certain rights in the invention.

FIELD OF THE INVENTION

The present invention relates generally to the field of dried vaccine compositions. More specifically, to methods of producing dried vaccine compositions bound to adjuvant and containing immunostimulatory molecules.

BACKGROUND OF THE INVENTION

Vaccines containing recombinant proteins benefit from or absolutely require an adjuvant to elicit an immune response. (Callahan et al., 1991, The importance of surface charge in the optimization of antigen-adjuvant interactions, Pharm. Res. 8(7):851-858; Singh and O'Hagan 1999, Advances in vaccine adjuvants, Nat Biotechnol 17(11): 1075-81; and O'Hagan et al., 2001, Recent developments in adjuvants for vaccines against infectious diseases, Biomol Eng 18(3): 69-85). Aluminum-salt adjuvants are currently the most widely used adjuvants for general use in humans because of the extensive history of safe use in vaccines administered to children and adults. The only adjuvants currently appearing in FDA-approved vaccines are the aluminum salt adjuvants, aluminum hydroxide and aluminum phosphate. Aluminum-salt adjuvants enhance the immunogenicity of vaccines and cause significant improvements in the outcomes of vaccination by reducing the dose level of protein in vaccine, elevating the titers of protective antibodies, and reducing the need for annual vaccination after a primary series of vaccination has been completed. Nonetheless, there are significant limitations in the use of aluminum-salt adjuvants in many subunit vaccines based on recombinant proteins, peptides, and chemically synthesized vaccines. These limitations include the general aspects of vaccine storage and stability, since vaccine containing aluminum adjuvants can be stored only within narrow temperature ranges, and cannot be frozen. Further limitations include the generally accepted view that aluminum adjuvants are relatively weak, do not foster the development of cellular immunity, and may favor the development of antibodies that are non-neutralizing in cases where neutralizing antibodies are necessary to block viral infections or impede the activity of biological toxins.

In the case of aluminum adjuvants, it has been suggested that to provide adequate immunogenicity, antigens must be adsorbed on the surface of the adjuvant. (Gupta et al., 1995, Adjuvant Properties of Aluminum and Calcium Compounds. Pharmaceutical Biotechnology. 6: 229-248; and White and Hem, 2000, Characterization of aluminium-containing adjuvants, Dev Biol (Basel) 103: 217-28). This adsorption is typically facilitated through electrostatic interactions between the antigen and adjuvant, and the formulation pH is usually chosen so that the antigen and adjuvant are oppositely charged (Callahan et al. 1991). The surface charge on the adjuvant also can be modified by surface exchange reactions with buffer salts such as phosphate, succinate, and citrate (Hem and White, 1984, Characterization of aluminum hydroxide for use as an adjuvant in parenteral vaccines. J Parenter Sci Technol, 38(1): p. 2-10; Chang et al., 1997, Role of the electrostatic attractive force in the adsorption of proteins by aluminum hydroxide adjuvant. PDA J Pharm Sci Technol, 51(1): p. 25-9; and Rinella et al., 1996, Treatment of aluminium hydroxide adjuvant to optimize the adsorption of basic proteins. Vaccine, 14(4): p. 298-300.) The mechanisms of action of aluminum-salt adjuvants are poorly understood, but likely due to several different mechanisms. (Lindblad 2004. "Aluminium compounds for use in vaccines" Immunol. Cell. Biol. 82(5):497-505; Gupta and Siber, 1995, Adjuvants for Human Vaccines—Current Status, Problems and Future-Prospects. Vaccine 13(14):1263-1276; Gupta and Rost, 2000, Aluminum Compounds as Vaccine Adjuvants, In O'Hagan D, editor Vaccine Adjuvants: Preparation Methods and Research Protocols, ed., Totowa, N.J.: Humana Press Inc. p 65-89; Cox and Coulter, 1997, Adjuvants—a classification and review of their modes of action, Vaccine 15(3):248-256). Common proposed mechanisms are that the adjuvant acts as a depot at the site of injection, wherein the antigen is slowly released after administration. (Cox and Coulter, 1997). Another proposed mechanism is that the adjuvant aids in delivery of the antigen to antigen-presenting cells (Lindblad 2004). A further proposed mechanism is that adjuvant serves as an immunostimulator and elicits Th2 cytokines (Grun and Maurer 1989, Different T helper cell subsets elicited in mice utilizing two different adjuvant vehicles: the role of endogenous interleukin 1 in proliferative responses. Cell Immunol 121(1):134-145). Yet another proposed mechanism is that adjuvant destabilizes protein antigens on the surface of the adjuvant making them more susceptible to proteolytic degradation (Jones et al., 2005, Effects of adsorption to aluminum salt adjuvants on the structure and stability of model protein antigens. J Biol Chem 280(14):13406-13414; and That et al., 2004. "Antigen stability controls antigen presentation" J. Biol. Chem. 279 (48):50257-50266).

Although the mechanism of action is not fully understood, it is likely that surface area, surface charge, and morphology of the adjuvant are important factors dictating the immune response to antigens adsorbed onto these adjuvants (Hem and White 1984). It is generally theorized that the smaller the particle size of the vaccine adjuvant, the more immunogenic the vaccine preparation, especially when particle size is approximately 1 micron, a size best suited for uptake into professional antigen presenting cells (Maa et al., 2003. Stabilization of alum-adjuvanted vaccine dry powder formulations: mechanism and application. J Pharm Sci 92(2): 319-332, Diminsky et al., 1999. Physical, chemical and immunological stability of CHO-derived hepatitis B surface antigen (HBsAg) particles. Vaccine 18(1-2):3-17).

Lyophilization (freeze drying) is a process frequently utilized to improve long term stability of various protein preparations. However, when vaccines formulated with aluminum-salt adjuvants are processed in an attempt to improve stability through freezing and lyophilization, a loss of potency occurs, where potency is a summation of the quality of the vaccine measurable by a series of tests that can include immunogenicity in animals, chemical degradation of protein antigen, denaturation of protein antigen, or loss of substituent immunogenic epitopes. Loss of potency is associated with loss of efficacy in humans. Previous studies have suggested that a freeze-dried vaccine product containing adjuvant cannot be produced due to aggregation of the adjuvant particles. (Diminsky et al., 1999; Maa et al., 2003). A number of theories have been set forth to explain possible mechanisms responsible for the loss of potency following lyophilization of vaccines formulated with aluminum-salt adjuvants. Particle aggregation may account for significant losses. For example, the aggregation of aluminum hydroxycarbonate and magnesium hydroxide gels after freezing and thawing has been attributed to ice crystal formation which forces particles together, resulting in irreversible aggregation. (Zapata et al., 1984, Mechanism of freeze-thaw instability of aluminum hydroxycarbonate and magnesium hydroxide gels. J Pharm Sci 73(1):3-8). This explanation has been proposed by Maa et al., 2003 suggesting further that faster cooling rates result in a greater rate of ice nucleation and the formation of smaller ice crystals, which would not force aluminum particles into an aggregate. Particle aggregation can thus account for losses of potency, but other factors, such as loss of protein configuration (tertiary structure), loss of protein secondary structure, and modifications of primary structure through deamidation or oxidation of amino acid side chains.

The capacity of particles to increase allergic sensitization is predicted by particle number and surface area, not by particle mass. Moorefield et al. showed that the degree of antigen internalization of adjuvant particles is inversely related to the particle size of the adjuvant aggregates (Moorefield et al., 2005. "Role of aluminum-containing adjuvants in antigen internalization by dendritic cells in vitro" Vaccine 23(13):1588-1595). Nygaard et al. showed that the particle diameter, and thus surface area and number of particles, and not mass or volume, is the dominant property in the immunological response of polystyrene particles in mice (Nygaard et al., 2004). While it is likely that the particle size is an important characteristic parameter for immunogenicity, there has yet to be a comprehensive study examining the particle size distribution (PSD) as a function of formulation and cooling rates along with other physical properties of the products produced.

There is some consensus view that the more effective vaccines with aluminum adjuvants are ones in which antigen is bound to the aluminum surface, rather than free in solution (Lindblad, 2004, Aluminium adjuvants—in retrospect and prospect, Vaccine, 22:3658-68). For reproducibility of formulations and stability, it is desirable to define conditions for optimal binding of antigen to crystal surfaces, and conditions in which antigen does not desorb over time or under elevated stress conditions. To construct aluminum vaccines, it is necessary to carry out studies to optimize binding and desorption. Aluminum adjuvants have a point of zero charge (PZC) at a certain solution pH, but are charged at pHs above or below this value (White and Hem, 2000, Characterization of aluminium-containing adjuvants, Dev Biol (Basel), 103: 217-28). Selecting an optimal formulation pH is further complicated for a recombinant protein vaccine for which binding to aluminum salt adjuvants is generally required to obtain the desired immune response (McInerney, Brennan et al., 1999, Analysis of the ability of five adjuvants to enhance immune responses to a chimeric plant virus displaying an HIV-1 peptide, Vaccine, 17:1359-68). To facilitate protein binding to adjuvant, a solution pH is selected in which the protein and adjuvant have opposite charges. However, a solution pH that provides optimal protein stability, may not allow for appropriate binding of the vaccine to adjuvants. In such a scenario, a vaccine protein may have to be prepared at pH that is suboptimal for stability and lyophilized with appropriate stabilizing excipients to minimize degradation during long-term storage.

Lyophilization of proteins to stabilize structure and activity for storage and reconstitution has been commonly applied to recombinant protein therapeutic proteins. This has been usually accomplished by freeze drying in the presence of disaccharides such as trehalose and other excipients that promote a glass state during process and storage. Proteins can be stored for long term as long as the product is stored below its glass transition temperature ($T_g$) above which the material transitions into a rubbery state. Excipients are thought to stabilize protein in the amorphous state through interactions of the stabilizer with specific sites substituting for water during drying and by simultaneously suppressing translational and rotational motions of the protein molecule ($\alpha$-relaxations) or portions of the molecule ($\beta$-relaxations). Drying technology has been less frequently applied to long term storage of vaccines, especially in the case of vaccines adsorbed to aluminum phosphate or aluminum hydroxide adjuvants. Very little data is available on the storage of dried vaccines under elevated temperature conditions, as most of the attempts to generate dried vaccines have been to obtain inhalable powders or preparations able to survive moderate excursions in temperature. For example, because the yellow fever vaccine is use primarily in tropical climates, lyophilization in the presence of stabilizers (lactose, sorbitol) has been used to preserve viability of the live virus vaccine (Monath, 1996, Stability of yellow fever vaccine, Dev Biol Stand, 87:219-25). Without excipients during lyophilization and storage, activity is rapidly lost above $-20°$ C., but the stabilized vaccine can withstand more than two weeks at $37°$ C. A lyophilized dried vaccine for the cattle disease rinderpest has also been developed and can be employed for up to a month after leaving the cold chain in African field conditions (House and Mariner, 1996, Stabilization of rinderpest vaccine by modification of the lyophilization process, Dev Biol Stand, 87:235-44). Similar attempts to use variations on process and drying have been recently applied to measles vaccine development (Burger, Cape et al., 2008, Stabilizing formulations for inhalable powders of live-attenuated measles virus vaccine, J Aerosol Med Pulm Drug Deliv, 21:25-34; Burger, Cape et al., 2008, Stabilizing Formulations for Inhalable Powders of Live-Attenuated Measles Virus Vaccine, J Aerosol Med) and for dried vaccine powders for influenza where it is likely very important to devise conditions that permit retention of the structure of the immunogen (Amorij, Meulenaar et al., 2007, Rational design of an influenza subunit vaccine powder with sugar glass technology: preventing conformational changes of haemagglutinin during freezing and freeze-drying, Vaccine, 25:6447-57; Amorij, Huckriede et al., 2008, Development of Stable Influenza Vaccine Powder Formulations: Challenges and Possibilities, Pharm Res). As a stabilizer, small amounts of formaldehyde are occasionally added to vaccines, including the current AVA anthrax vaccine (Biothrax®), and may act by cross-linking proteins forming more immunogenic protein aggregates on the surface of aluminum crystals (Little, Ivins et al., 2007, Effect of aluminum hydroxide adjuvant and formaldehyde in the formulation of rPA anthrax vaccine, Vaccine, 25:2771-7). Formaldehyde had been used historically as the stabilizer of choice in the older vaccines derived from culture supernatants, such as tetanus toxoid, botulinum toxoids, and others. The current AVA vaccine is labeled for 3 year stability, where stability is a function of a number of biochemical evaluations and potency. Although a moderate amount of stability can be achieved with liquid suspension vaccines, it is not likely that all stability parameters can be met for longer storage periods that are required for vaccines to be stockpiled and distributed.

Successful drying of therapeutic proteins, while retaining structure and function, is dependent on the knowledge of the degradation pathways that occur in solution, which can be retarded or eliminated by appropriate drying and excipients for stabilization. For vaccines, function is largely determined by immunogenicity and protection studies, rather than enzymatic activity. In the case of protein immunogens that are adsorbed to aluminum adjuvants crystals, the measurement of function and other parameters in vitro is correspondingly more difficult, since protein may be sequestered and difficult to remove for analysis. Thus, function can only be tested by immunogenicity and protection studies. The tertiary conformation of proteins can obviously affect enzymatic functions, if present, but also can affect immunogenicity of B cell epitopes dependent on conformation. Linear B and T cell epitopes contained therein can be also affected by oxidation (of methionine and cysteine residues) and deamidation (especially of asparagine residues). pH is one of the most critical formulation variables governing stability of therapeutic proteins. (Carpenter, Chang et al., 2002, Rational design of stable lyophilized protein formulations: theory and practice, Pharm Biotechnol, 13:109-33; Chi, Krishnan et al., 2003, Physical stability of proteins in aqueous solution: mechanism and driving forces in nonnative protein aggregation, Pharm Res, 20:1325-36) By affecting the conformational and colloidal stability of proteins in solution, pH can greatly modulate their aggregation rates (Chi, Krishnan et al., 2003, Physical stability of proteins in aqueous solution: mechanism and driving forces in nonnative protein aggregation, Pharm Res, 20:1325-36). In addition, rates of deamidation are strongly dependent on pH (Manning, Patel et al., 1989, Stability of protein pharmaceuticals, Pharm Res, 6:903-18). There can be different optimal pH values for physical and chemical stability for a given protein (Kolvenbach, Narhi et al., 1997, Granulocyte-colony stimulating factor maintains a thermally stable, compact, partially folded structure at pH2, J Pept Res, 50:310-8). For example, physical stability may be optimal at a pH where deamidation is unacceptably rapid (Chang, Reeder et al., 1996, Development of a stable freeze-dried formulation of recombinant human interleukin-1 receptor antagonist, Pharm Res, 13:243-9). In such cases, development of a lyophilized formulation where the rates of these reactions are minimized may provide a viable strategy to obtain a stable product. The few published studies examining effects of pre-lyophilization solution pH on the stability of therapeutic proteins during lyophilization and storage in dried formulations demonstrated the importance of this parameter (Prestrelski, Pikal et al., 1995, Optimization of lyophilization conditions for recombinant human interleukin-2 by dried-state conformational analysis using Fourier-transform infrared spectroscopy, Pharm Res, 12:1250-9; Chang, Reeder et al., 1996, Development of a stable freeze-dried formulation of recombinant human interleukin-1 receptor antagonist, Pharm Res, 13:243-9; Katayama, Kirchhoff et al., 2004, Retrospective statistical analysis of lyophilized protein formulations of progenipoietin using PLS: determination of the critical parameters for long-term storage stability, J Pharm Sci, 93:2609-23). These studies demonstrated the difficulty in identifying a pre-lyophilization solution pH that confers adequate physical and chemical stability to the proteins studied during lyophilization and storage. However, degradation of proteins could be minimized if sufficient amounts of stabilizing excipients are included in the formulation. For example, when recombinant human interleukin-1-receptor antagonist (rhIL-1ra) was formulated prior to lyophilization in a solution containing suboptimal sucrose at levels less than 0.3 mass ratio of sucrose/protein and at pH less than 6.5, severe protein aggregation occurred after lyophilization, during storage and reconstitution (Chang, Reeder et al., 1996, Development of a stable freeze-dried formulation of recombinant human interleukin-1 receptor antagonist, Pharm Res, 13:243-9). Protein aggregation was minimized following lyophilization from a solution at pH greater than 6, although, deamidation occurred at an unacceptably high rate. Following lyophilization from a solution containing amounts of sucrose greater than 0.3 sucrose/protein mass ratio at pH 6.5, both destabilization pathways could be inhibited. In another example, interleukin-2 (IL-2) had significantly greater structural perturbation during freeze-drying at pH 7, which resulted in higher levels of aggregation after storage and rehydration than samples lyophilized from solutions at pH 5 (Prestrelski, Pikal et al., 1995, Optimization of lyophilization conditions for recombinant human interleukin-2 by dried-state conformational analysis using Fourier-transform infrared spectroscopy, Pharm Res, 12:1250-9). The addition of sucrose to the pre-lyophilization solution formulation at pH 7 improved the stability of IL-2 during storage following lyophilization. More recently, this approach to pre-formulation has been taken with anthrax rPA to create a dried powder vaccine candidate for nasal administration (Jiang, Joshi et al., 2006, Anthrax vaccine powder formulations for nasal mucosal delivery, J Pharm Sci, 95:80-96). In this case, conditions for optimizing pH and excipient stabilizers were established for rPA in solution prior to lyophilization. As trehalose was one of the excipients determined to stabilize soluble rPA to thermal stress, there was evidence of at least 30 days stability at 40° C. for the dried trehalose-containing vaccines in terms of the total content of rPA in comparison to liquid samples in which rPA quickly disappeared. In an effort to obtain a dried powder composition for epidermal delivery using a gas-driven injection device, it was found that rapid freezing of aluminum-adsorbed hepatitis B vaccine (HBsAg) in the presence of a mixture of mannitol, glycine, and dextran (not more than ~6% w/v of total excipients) resulted in vaccines that retained particle size and relative immunogenicity in mice after a rapid freezing (spray freeze drying) that involved injection of the sprayed vaccine into liquid nitrogen prior to drying (Maa, Zhao et al., 2003, Stabilization of alum-adjuvanted vaccine dry powder formulations: mechanism and application, J Pharm Sci, 92:319-32). The behavior of the spray-freeze dried vaccines under thermal stress conditions was not determined, although normally lyophilized vaccine aggregated after processing and was minimally immunogenic. Diminished immunogenicity was associated with aluminum particle aggregation after reconstitution.

More lately, Roser et al. have suggested lyophilization methods that will prevent aggregation of aluminum particles. Roser et al., U.S. Pat. No. 6,890,512 disclose a method of preventing gross aggregation during dehydration and rehydration of particulates in suspension by adding to a particulate suspension of aluminum hydroxide in excess of 15% (w/v) of trehalose. Trehalose, alpha.-D-glucopyranosyl-alpha-D-glucopyranoside, is a naturally occurring disaccharide responsible for protection of plant cells from desiccation. Trehalose has been shown to prevent denaturation of proteins during desiccation by forming sugar glasses that immobilize protein structure. However, Roser et al., while disclosing prevention of gross particle aggregation, do not disclose the importance of freezing rate of a particulate suspension or other factors critical to control and maintain pre-lyophilization particle size and protein structure in an aluminum-salts containing vaccine in the presence of trehalose. Maintenance of particle size is a critical parameter in controlling the degree of adsorption of protein immunogens to the surface of aluminum particles, and is influenced by several factors during lyophilization cycle in addition to the content of trehalose or other glassifying excipients. These factors influence the immunogenicity and generation of protective immune responses.

Aluminum-salt adjuvants provide a well explored means to augment the immunogenicity of protein or peptide subunit vaccines. However, a variety of exploratory formulations to enhance vaccines have been developed as more potent alternative to aluminum-salts adjuvants, but are not currently available in FDA-licensed human vaccines. Formulations designed to enhance immune responses include a variety of compositions based on water-in-oil emulsions, oil-in-water emulsions, self-assembling macrostructures, cytokines, saponins, toll-like receptor agonists (TLR-4, TLR-5, and TLR-9), immunostimulatory double stranded RNA species, unmethylated DNA oligonucleotides, and polymeric microparticles and nanostructures. Many of these compositions are directed towards improving the immunogenicity of injected vaccines, and some variations can be applied to altering routes of delivery for intranasal or oral vaccination. As an example of one class of immunostimulatory molecules that can be used to enhance vaccine immunogenicity, bacterial DNA, but not vertebrate DNA, can be used because of direct immunostimulatory effects that activate lymphocytes. This is due to unmethylated CpG dinucleotides are present at the expected frequency in bacterial DNA but are under-represented and methylated in vertebrate DNA (Krieg et al., 1995). Activation may also be triggered by addition of synthetic oligodeoxynucleotides (ODN) that contain an unmethylated CpG dinucleotide in a particular sequence context. CpG DNA induces proliferation of almost all (>95%) B cells and increases immunoglobulin (Ig) secretion. This B cell activation by CpG DNA is T cell independent and antigen non-specific. However, B cell activation by low concentrations of CpG DNA has strong synergy with signals delivered through the B cell antigen receptor for both B cell proliferation and Ig secretion (Krieg et al., 1995). This strong synergy between the B cell signaling pathways triggered through the B cell antigen receptor and by CpG DNA promotes antigen specific immune responses. In addition to its direct effects on B cells, CpG DNA also directly activates monocytes, macrophages, and dendritic cells to secrete a variety of cytokines, including high levels of IL-12 (Klinman et al., 1996; Halpern et al., 1996; Cowdery et al., 1996). These cytokines stimulate natural killer (NK) cells to secrete gamma-interferon (IFN-.gamma.-) and have increased lytic activity (Klinman et al., 1996, supra; Cowdery et al., 1996, supra; Yamamoto et al., 1992; Ballas et al., 1996). Overall, CpG DNA induces a Th1 like pattern of cytokine production dominated by IL-12 and IFN-gamma with little secretion of Th2 cytokines (Klinman et al., 1996). Other molecules stimulate toll like receptors. One example is flagellin, the protein subunit comprising numerous bacterial flagella. Flagellin is a TLR-5 ligand and triggers at least one of the biological functions of antigen presenting cells upon such binding. Flagella are found on the surface of rod and spiral shaped bacteria, including members of the genera *Escherichia, Salmonella, Proteus, Pseudomonas, Bacillus, Campylobacter, Vibrio, Treponema, Legionella, Clostridia*, and *Caulobacter*. The conserved regions of flagellins are important for TLR5 binding, while the polymorphic central region can be deleted without affecting binding to TLR5. Flagellin sequences from numerous bacteria are available in the art, such as Genbank accession numbers D13689, YP.sub.—275549, YP.sub.—275550, AAU18718, AAU18717, ZP.sub.—00743095, EA052626, YP.sub.—315348, AAT28337, AAT28336, AAT28335, AAT28334, AAT28333, AAZ36356, AAZ33167, AAZ94424, AAZ91670, NP.sub.—414908, BAD18052, and BAD18051. As a third example of purified adjuvant immune stimulants, non toxic chemically synthesized or enzymatically modified derivatives of gram negative lipopolysaccharides are potent adjuvants and act by stimulating lymphocytes through TLR-4 binding and activation. For example, monophosphoryl lipid A (MPL) is a derivative of the lipid A component of lipopolysaccharide and is a potent activator of pro-inflammatory cytokines. Although native lipid A and its parent LPS have powerful pyrogenic properties and in humans induce febrile responses (Greisman and Homick, J Immunol, 109:1210-1215 (1972); Greisman and Homick, J Infect Dis, 128:257-263 (1973); Abemathy and Spink, J Clin Invest, 37:219-225 (1958); Rietschel et al, supra; and Raetz, supra (1993)), MPL and its chemically synthesized analogues are not toxic but induce a compendium of host proinflammatory cytokines including IL-1, IL-6, and TNF-alpha.

In addition, to enhance the immune response to subunits adsorbed to aluminum salts, it is likely that co-adjuvants will be required in order to generate effective antibody responses in humans after one or two doses. A number of adjuvant compounds that are compatible with aluminum salts have been evaluated as adjuvants in recent years. Primarily these adjuvants include Monophosphoryl Lipid A (MPL) and QS-21, and CpG sequences. Recent data with anthrax vaccine indicates in human studies that AVA, an AlOH adsorbed vaccine, can be significantly enhanced by adding CpG 7909 to the adjuvant formulations in non-human primates and humans, in terms of total anti-rPA antibodies and anthrax toxin neutralizing antibodies, although no data describe the long term thermal stability of CpG-containing vaccines (Klinman, 2006, CpG oligonucleotides accelerate and boost the immune response elicited by AVA, the licensed anthrax vaccine, Expert Rev Vaccines, 5:365-9). MPL and QS-21 have been also used with aluminum salts as well as in proprietary oil emulsion formulations being developed by Glaxo Smith Kline Biologics. QS-21 has been evaluated in AlOH vaccines in humans and animal models with good evidence of tolerability and systemic safety. QS-21 is thought to bind to aluminum salts through ionic and hydrophobic interactions, as well as some part of it remaining in solution (in aqueous vaccines) in a micellar form. QS-21 is a saponin purified from tree bark with broad adjuvant effects to induce both antibody and cell mediated immunity. Though the mechanism is not understood, dose levels effective in conjunction with human vaccines have been evaluated. QS-21 with aluminum has been evaluated in clinical studies and independent safety studies of QS-21 formulated with antigens have been studied. QS-21 has been associated with stinging at the site of injection (that resolves), with very little evidence of systemic side effects (Waite, Jacobson et al., 2001, Three double-blind, randomized trials evaluating the safety and tolerance of different formulations of the saponin adjuvant QS-21, Vaccine, 19:3957-67). Several studies in humans have shown that QS-21 enhances responses to antigens that are adsorbed to aluminum. These include several trials in malaria vaccine candidates (Nardin, Oliveira et al., 2000, Synthetic malaria peptide vaccine elicits high levels of antibodies in vaccinees of defined HLA genotypes, J Infect Dis, 182:1486-96; Kashala, Amador et al., 2002, Safety, tolerability and immunogenicity of new formulations of the *Plasmodium falciparum* malaria peptide vaccine SPf66 combined with the immunological adjuvant QS-21, Vaccine, 20:2263-77), HIV gp120 (Evans, McElrath et al., 2001, QS-21 promotes an adjuvant effect allowing for reduced antigen dose during HIV-1 envelope subunit immunization in humans, Vaccine, 19:2080-91) and more recently Rhesus macaque trials of Dengue virus subunits in which neutralizing titers and protection were enhanced by QS-21 (Putnak, Coller et al., 2005, An evaluation of dengue type-2 inactivated, recombinant subunit, and live-attenuated vaccine candidates in the rhesus macaque model, Vaccine, 23:4442-52). The solution stability of QS-21 has been well studied under long term stability studies, and has shown that adjuvant active QS-21 (which actually consists of two isomeric forms) is highly stable in slightly acidic buffers for over 4 years, whereas less than 10 days at 40° C. (Kensil and Kammer, 1998, QS-21: a water-soluble triterpene glycoside adjuvant, Expert Opin Investig Drugs, 7:1475-82). QS-21 is stored as a dried powder and in that form is stable indefinitely.

Ricin toxin is a 64 kDa protein produced by castor beans (Ricinus communis) (Doan L G. Ricin: mechanism of toxicity, clinical manifestations, and vaccine development. A review. Journal of Toxicology—Clinical Toxicology 2004; 42(2):201-8; Audi J, Belson M, Patel M, Schier J, Osterloh J. Ricin poisoning: a comprehensive review. JAMA 2005; 294(18):2342-51). The holotoxin consists of two polypeptide chains (A and B) joined by a disulfide bond. The A chain (RTA) is a ribosome inactivating protein (RIP) that inhibits protein synthesis in mammalian cells. The B chain (RTB) is a lectin that binds to galactose residues on the surface of cells. Once internalized by a cell, RTA translocates into the cytosol where it enzymatically inactivates 60S ribosomes (Smallshaw, J E and Vitetta, E S, A lyophilized formulation of RiVax, a recombinant ricin subunit vaccine, retains immunogenicity. Vaccine 2010 Mar. 11; 28(12): 2428-2435). A single molecule of RTA in the cytoplasm of a cell completely inhibits protein synthesis. The reported estimated lethal dose of ricin in humans is 1-25 µg/kg when inhaled, injected, or ingested (Audi et al). Because of its wide availability and extraordinary toxicity, ricin represents a potential agent for use in bioterrorism and is therefore classified by the Centers for Disease Control, Atlanta Ga. (CDC) as a level B biothreat. Ricin intoxication can be prevented in experimental animals by vaccination with toxoid or deglycosylated ricin A chain (dgRTA), or by passive immunization with anti-ricin antibodies. However the toxoid is considered to be too toxic for routine use in humans and dgRTA is difficult and expensive to produce, and also retains both active sites and could induce toxic side effects in humans. Passive immunization with anti-ricin antibodies is only effective if the ricin dose is relatively low and the antibody is administered within a few hours after exposure (Hewetson J F, Rivera V R, Creasia D A, Lemley P V, Rippy M K, Poli M A. Protection of mice from inhaled ricin by vaccination with ricin or by passive treatment with heterologous antibody. Vaccine 1993; 11(7):743-6).

In order to avoid these limitations, a recombinant RTA vaccine (RiVax) was developed (Smallshaw et al.). RiVax incorporated two point mutations, Y80A and V76M, to greatly reduce or eliminate both of its known toxicities, i.e. ribotoxicity and vascular leak-inducing ability. In the absence of adjuvant, RiVax is non-toxic and immunogenic in mice, rabbits and humans (Smallshaw J E, Firan A, Fulmer J R, Ruback S L, Ghetie V, Vitetta E S. A novel recombinant vaccine which protects mice against ricin intoxication. Vaccine 2002; 20(27-28):3422-7). Such a model has been showed to yield positive results without much of the toxicity implicated with other vaccine models.

Ricin is currently listed by NIAID and the Centers for Disease Control and Prevention (CDC) as a level B Biothreat agent (Rotz, Khan et al., 2002, Public health assessment of potential biological terrorism agents, Emerging Infectious Diseases, 8:225-30.). The vaccine candidate is based on a recombinant subunit vaccine against ricin toxin obtained by genetic inactivation of residues in the ricin toxin A chain (RTA) that are involved in well characterized activities of the molecule. This modified molecule is immunogenic in mice, rabbits, and humans and induces antibodies that neutralize the toxin or are involved with clearance of the toxin systemically or mucosally in each species. In the case of smallpox or anthrax, terrorist induced epidemics could be controlled by mass vaccination, selective vaccination, or ring vaccination after evidence of an outbreak (Halloran, Longini et al., 2002, Containing bioterrorist smallpox, Science, 298:1428-32; Kaplan, Craft et al., 2002, Emergency response to a smallpox attack: the case for mass vaccination, Proc Natl Acad Sci USA, 99:10935-40; Bozzette, Boer et al., 2003, A model for a smallpox-vaccination policy, N Engl J Med, 348:416-25; Kretzschmar, van den Hof et al., 2004, Ring vaccination and smallpox control, Emerg Infect Dis, 10:832-41). On the other hand, vaccination against bioterrorist exposure to biological toxins, because the agents do not replicate, is more likely to be used in select populations, such as the military or first responders, rather than mass vaccination. The isolated A and B subunit of ricin can be produced in *E. coli* and other recombinant hosts. The B chain is also a candidate for inclusion in a vaccine, but is considered less immunogenic and less protective than the A chain (Maddaloni, Cooke et al., 2004, Immunological characteristics associated with the protective efficacy of antibodies to ricin, Journal of Immunology, 172:6221-8). Although ricin A chain is at least 1000-fold less toxic than the native ricin, it still retains enzymatic activity that may result in toxicity when used as a vaccine (Thorpe, Detre et al., 1985, Modification of the carbohydrate in ricin with metaperiodate-cyanoborohydride mixtures. Effects on toxicity and in vivo distribution, European Journal of Biochemistry, 147: 197-206.). Several key amino acid residues in ricin A chain, Y80, Y123, E177, R180, N209, and W211, constitute its enzymatically-active site (Olson, 1997, Ricin A-chain structural determinant for binding substrate analogues: a molecular dynamics simulation analysis, Proteins, 27:80-95; Lebeda and Olson, 1999, Prediction of a conserved, neutralizing epitope in ribosome-inactivating proteins, International Journal of Biological Macromolecules, 24:19-26). Mutations in some of these amino acid residues have yielded ricin A chains with negligible toxicity as determined by the inhibition of protein synthesis (Kim and Robertus, 1992, Analysis of several key active site residues of ricin A chain by mutagenesis and X-ray crystallography, Protein Engineering, 5:775-9.). An additional site and residues involved in the binding of RTA to endothelial cells have also been identified, which occur extracellularly and do not require toxin entry into host cells (Baluna and Vitetta, 1999, An in vivo model to study immunotoxin-induced vascular leak in human tissue, J Immunother, 22:41-7; Baluna, Coleman et al., 2000, The effect of a monoclonal antibody coupled to ricin A chain-derived peptides on endothelial cells in vitro: insights into toxin-mediated vascular damage, Exp Cell Res, 258:417-24; Smallshaw, Ghetie et al., 2003, Genetic engineering of an immunotoxin to eliminate pulmonary vascular leak in mice, Nature Biotechnology, 21:387-91). The endothelial binding site on RTA is implicated in the damage to isolated HUVEC cells and to the induction of vascular leak syndrome (VLS), which has been determined to be a dose limiting toxicity in the use of RTA-containing immunotoxins (Smallshaw, Ghetie et al., 2003, Genetic engineering of an immunotoxin to eliminate pulmonary vascular leak in mice, Nature Biotechnology, 21:387-91). The portion of RTA involved in both pulmonary vascular leak, vascular leak in human skin xenografts in SCID mice, and HUVEC cells appears to involve amino acid residues L74, D75, and V76 (Baluna, Rizo et al., 1999, Evidence for a structural motif in toxins and interleukin-2 that may be responsible for binding to endothelial cells and initiating vascular leak syndrome, Proceedings of the National Academy of Sciences of the United States of America, 96:3957-62.). Therefore, an A chain vaccine taking into account those toxic sites has been constructed and comprises a double mutant of ricin A chain. Tyrosine 80 is mutated to alanine in the enzymatic site and valine 76 is mutated to methionine in the vascular leak site to minimize any possible in endothelial cell damage. It is known now based on crystal structure data that this protein is identical in structure to native ricin A chain (RTA), indicating that the point mutations contained in the molecule do not disrupt any potential tertiary structure (or potential conformationally-dependent epitopes). When administered intramuscularly (i.m.) to mice in the absence of adjuvant, the mutant A chain elicited antibodies that recognized ricin and animals were protected from a $10 \times LD_{50}$ dose of ricin (Smallshaw, Firan et al., 2002, A novel recombinant vaccine which protects mice against ricin intoxication, Vaccine, 20:3422-7.).

Native PA is the dominant immunogen in AVA (anthrax vaccine adsorbed) and target for protective immunity in pre-exposure and post exposure prophylaxis as a single component vaccine. Several aluminum adsorbed recombinant PA vaccines ($2^{nd}$ generation), based on expression of native PA in avirulent *B. anthracis*, have been advanced and tested in recent Phase I trials, and have been shown to be immunogenic in relationship to AVA (Gorse, Keitel et al., 2006, Immunogenicity and tolerance of ascending doses of a recombinant protective antigen (rPA102) anthrax vaccine: a randomized, double-blinded, controlled, multicenter trial, Vaccine, 24:5950-9; Campbell, Clement et al., 2007, Safety, reactogenicity and immunogenicity of a recombinant protective antigen anthrax vaccine given to healthy adults, Hum Vaccin, 3:205-11). The major correlates of immunity have been well characterized in rabbit aerosol spore challenge studies (total ELISA-reactive antibodies and toxin neutralizing activity (TNA))(Little, Ivins et al., 2004, Defining a serological correlate of protection in rabbits for a recombinant anthrax vaccine, Vaccine, 22:422-30). It is well known that anthrax toxin is a tripartite toxin consisting of a set of three plasmid-encoded proteins expressed by *B. anthracis*: Protective Antigen (PA; 83 kDa), Lethal Factor (LF; 90 kDa) and Edema Factor (EF; 89 kDa). LF and EF are transported from the extracellular surface into the cytoplasm by the heptamerized PA where they act by enzymatically modifying molecular targets of mammalian cells. LF is a metalloprotease that cleaves and activates several mitogen-activated protein kinases (MAPK kinases) and EF is a calmodulin-dependent adenylate cyclase that causes a rapid increase in intracellular cAMP levels. (Young and Collier, 2007, Anthrax toxin: receptor binding, internalization, pore formation, and translocation, Annu Rev Biochem, 76:243-65). These proteins are nontoxic individually, but when administered together are a potent toxin, causing rapid cell death.

The AVA vaccine is still the only vaccine for anthrax and the major move to improve on it is based on several perceived shortcomings: requirement for a 6-dose regimen in order to achieve solid immunity and the perception that it is unsafe and reactogenic, and that the preparative processing of AVA is crude and lacks consistency. Although PA is the major immunogen in AVA, it is not clear whether the small amounts of LF and EF that may be present in some lots contribute to the vaccine's effectiveness. A major factor in loss of immunogenicity of anthrax rPA involves accelerated deamidation on the adjuvant surface. This could be prevented by the presence of small amounts of phosphate to lower the surface pH. There are other particular rPA vaccine candidates that are being developed. AVA or PA-based vaccines in general induce toxin neutralizing antibodies (Pitt, Little et al., 1999, In vitro correlate of immunity in an animal model of inhalational anthrax, J Appl Microbiol, 87:304; Reuveny, White et al., 2001, Search for correlates of protective immunity conferred by anthrax vaccine, Infect Immun, 69:2888-93; Little, Ivins et al., 2004, Defining a serological correlate of protection in rabbits for a recombinant anthrax vaccine, Vaccine, 22:422-30). The mechanism underlying the protective action of PA-based vaccines is attributable to anti-PA antibodies that protect the host from intoxication and thus allow the immune system to deal with the organism, though PA vaccine is not designed to limit the onset of infection.

There are 72 vaccines presently approved by FDA in the United States (U.S. Food and Drug Administration. Complete List of Vaccines Licensed for Immunization and Distribution in the US. FDA. Jun. 3, 2010). Of these 72 vaccines, 36% contain an aluminum adjuvant and 30% are freeze dried. None of the 72 vaccines contain both an aluminum adjuvant and freeze dried component.

There is a need in the art to develop methods of producing thermostable, immunologically-active freeze dried vaccine preparations which incorporates recombinant antigens to promote rapid onset of protective immunity.

SUMMARY OF THE INVENTION

The disclosure provides a method of production of thermostable, freeze dried vaccine adjuvant-containing preparations. The disclosure further provides a method of production of thermostable, freeze dried vaccine preparations in which the vaccine antigens are recombinant antigens.

In one embodiment, the disclosure provides a method of preparing an immunologically-active adjuvant-bound dried vaccine composition, the method comprising: combining at least one aluminum-salt adjuvant, at least one buffer system containing at least one volatile salt, at least one glass-forming agent, at least one immunologically active co-adjuvant and at least one antigen to create a liquid vaccine formulation; freezing the liquid vaccine formulation to create a frozen vaccine formulation; and lyophilizing the frozen vaccine formulation to create a dried vaccine composition, where the composition is capable of eliciting an immune response in a subject. The immune response developed by the subject may be humoral immunity and/or cell-mediated immunity specific to the antigen. In one aspect, the at least one aluminum-salt adjuvant is selected from the group consisting of aluminum hydroxide, aluminum phosphate and aluminum sulfate. In another aspect, the aluminum-salt adjuvant is aluminum hydroxide. In a further aspect, the at least one buffer system is selected from the group consisting of acetate, succinate, citrate, prolamine, arginine, glycine, histidine, borate, carbonate and phosphate buffer systems. In yet another aspect, the at least one buffer system is selected from the group consisting of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate. In another aspect, the at least one glass-forming agent is selected from the group consisting of trehalose, sucrose, ficoll, dextran, sucrose, maltotriose, lactose, mannitol, hydroxyethyl starch, glycine, cyclodextrin, and povidone. In a further aspect, the glass-forming agent is trehalose. In one aspect, the glass-forming agent trehalose is present in a weight-to-volume concentration of from about 5% to about 15% in the liquid vaccine formulation prior to freeze drying. In another aspect, the glass-forming agent trehalose is present in a weight-to-volume concentration from about 8% to about 20% in the liquid vaccine formulation. In another embodiment, at least one immunologically-active co-adjuvant is added to the method steps. In this aspect, the at least one immunologically-active co-adjuvant is selected from the group consisting of lipid A, lipid A derivatives, monophosphoryl lipid A, chemical analogues of monophosphoryl Lipid A, CpG containing oligonucleotides, TLR-4 agonists, flagellin, flagellins derived from gram negative bacteria, TLR-5 agonists, fragments of flagellins capable of binding to TLR-5 receptors, saponins, analogues of saponins, QS-21, purified saponin fractions, ISCOMS, saponin combinations with sterols and lipids. In a further aspect, the co-adjuvant compound is QS-21. In a further aspect, the freezing step comprises one of tray freezing, shelf freezing, spray-freezing and shell-freezing. In preferred embodiment, the freezing step includes use of a pre-cooled tray to initiate the freezing step.

In another aspect, the antigen is selected from or derived from the group consisting of rotavirus, foot and mouth disease virus, influenza A virus, influenza B virus, influenza C virus, H1N1, H2N2, H3N2, H5N1, H7N7, H1N2, H9N2, H7N2, H7N3, H10N7, human parainfluenza type 2, herpes simplex virus, Epstein-Barr virus, varicella virus, porcine herpesvirus 1, cytomegalovirus, lyssavirus, *Bacillus anthracis*, anthrax PA and derivatives, poliovirus, Hepatitis A, Hepatitis B, Hepatitis C, Hepatitis E, distemper virus, venezuelan equine encephalomyelitis, feline leukemia virus, reovirus, respiratory syncytial virus, Lassa fever virus, polyoma tumor virus, canine parvovirus, papilloma virus, tick borne encephalitis virus, rinderpest virus, human rhinovirus species, *Enterovirus* species, Mengovirus, paramyxovirus, avian infectious bronchitis virus, human T-cell leukemia-lymphoma virus 1, human immunodeficiency virus-1, human immunodeficiency virus-2, lymphocytic choriomeningitis virus, parvovirus B19, adenovirus, rubella virus, yellow fever virus, dengue virus, bovine respiratory syncitial virus, corona virus, *Bordetella pertussis, Bordetella bronchiseptica, Bordetella parapertussis, Brucella abortis, Brucella melitensis, Brucella suis, Brucella ovis, Brucella* species, *Escherichia coli, Salmonella* species, *Salmonella typhi*, Streptococci, *Vibrio cholera, Vibrio parahaemolyticus, Shigella, Pseudomonas,* tuberculosis, avium, Bacille Calmette Guerin, *Mycobacterium leprae,* Pneumococci, Staphlylococci, *Enterobacter* species, *Rochalimaia henselae, Pasteurella haemolytica, Pasteurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia rickettsii, Rickettsia typhi, Rickettsia prowsaekii, Ehrlichia chaffeensis, Anaplasma phagocytophilum, Plasmodium falciparum, Plasmodium vivax, Plasmodium malariae, Schistosomes,* trypanosomes, *Leishmania* species, *Filarial nematodes,* trichomoniasis, sarcosporidiasis, *Taenia saginata, Taenia solium, Leishmania, Toxoplasma gondii, Trichinella spiralis,* coccidiosis, *Eimeria tenella, Cryptococcus neoformans, Candida albican, Apergillus fumigatus,* coccidioidomycosis, *Neisseria gonorrhoeae,* malaria circumsporozoite protein, malaria merozoite protein, trypanosome surface antigen protein, pertussis, alphaviruses, adenovirus, diphtheria toxoid, tetanus toxoid, meningococcal outer membrane protein, streptococcal M protein, Influenza hemagglutinin, cancer antigen, tumor antigens, toxins, *Clostridium perfringens* epsilon toxin, ricin toxin, *Pseudomonas* exotoxin, exotoxins, neurotoxins, cytokines, cytokine receptors, monokines, monokine receptors, plant pollens, animal dander, and dust mites.

In another embodiment, the disclosure provides a vaccine composition, comprising: at least one aluminum-salt adjuvant; at least one buffering agent, wherein the at least one buffering agent comprises a volatile salt; at least one glass forming agent; and at least one antigen, wherein the composition is lyophilized to create a dried vaccine composition and further wherein the dried vaccine composition is capable of eliciting an immune response in a subject. In one aspect, the at least one aluminum-salt adjuvant is selected from the group consisting of aluminum hydroxide, aluminum phosphate and aluminum sulfate. In another aspect, the at least one buffering agent is selected from the group consisting of acetate, succinate, citrate, prolamine, arginine, glycine, histidine, borate, carbonate and phosphate. In an alternative aspect, the at least one buffering agent is selected from the group consisting of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate. In yet another aspect, the at least one glass-forming agent is selected from the group consisting of trehalose, sucrose, ficoll, dextran, sucrose, maltotriose, lactose, mannitol, hydroxyethyl starch, glycine, cyclodextrin, and povidone. In a further aspect, the antigen is selected from or derived from the group consisting of rotavirus, foot and mouth disease virus, influenza A virus, influenza B virus, influenza C virus, H1N1, H2N2, H3N2, H5N1, H7N7, H1N2, H9N2, H7N2, H7N3, H10N7, human parainfluenza type 2, herpes simplex virus, Epstein-Barr virus, varicella virus, porcine herpesvirus 1, cytomegalovirus, lyssavirus, *Bacillus anthracis*, anthrax PA and derivatives, poliovirus, Hepatitis A, Hepatitis B, Hepatitis C, Hepatitis E, distemper virus, venezuelan equine encephalomyelitis, feline leukemia virus, reovirus, respiratory syncytial virus, Lassa fever virus, polyoma tumor virus, canine parvovirus, papilloma virus, tick borne encephalitis virus, rinderpest virus, human rhinovirus species, *Enterovirus* species, Mengovirus, paramyxovirus, avian infectious bronchitis virus, human T-cell leukemia-lymphoma virus 1, human immunodeficiency virus-1, human immunodeficiency virus-2, lymphocytic choriomeningitis virus, parvovirus B19, adenovirus, rubella virus, yellow fever virus, dengue virus, bovine respiratory syncitial virus, corona virus, *Bordetella pertussis, Bordetella bronchiseptica, Bordetella parapertussis,*

*Brucella abortis, Brucella melitensis, Brucella suis, Brucella ovis, Brucella* species, *Escherichia coli, Salmonella* species, *Salmonella typhi*, Streptococci, *Vibrio cholera, Vibrio parahaemolyticus,* Shigella, *Pseudomonas,* tuberculosis, avium, Bacille Calmette Guerin, *Mycobacterium leprae,* Pneumococci, Staphlylococci, *Enterobacter* species, *Rochalimaia henselae, Pasteurella haemolytica, Pasteurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia rickettsii, Rickettsia typhi, Rickettsia prowsaekii, Ehrlichia chaffeensis, Anaplasma phagocytophilum, Plasmodium falciparum, Plasmodium vivax, Plasmodium malariae, Schistosomes, trypanosomes, Leishmania* species, *Filarial nematodes,* trichomoniasis, sarcosporidiasis, *Taenia saginata, Taenia solium, Leishmania, Toxoplasma gondii, Trichinella spiralis,* coccidiosis, *Eimeria tenella, Cryptococcus neoformans, Candida albican, Apergillus fumigatus,* coccidioidomycosis, *Neisseria gonorrhoeae,* malaria circumsporozoite protein, malaria merozoite protein, trypanosome surface antigen protein, pertussis, alphaviruses, adenovirus, diphtheria toxoid, tetanus toxoid, meningococcal outer membrane protein, streptococcal M protein, Influenza hemagglutinin, cancer antigen, tumor antigens, toxins, *Clostridium perfringens* epsilon toxin, ricin toxin, *Pseudomonas* exotoxin, exotoxins, neurotoxins, cytokines, cytokine receptors, monokines, monokine receptors, plant pollens, animal dander, and dust mites.

In an alternative embodiment, the vaccine composition further includes at least one immunologically-active co-adjuvant. In one aspect, the at least one immunologically-active co-adjuvant is selected from the group consisting of lipid A, lipid A derivatives, monophosphoryl lipid A, chemical analogues of monophosphoryl Lipid A, CpG containing oligonucleotides, TLR-4 agonists, flagellin, flagellins derived from gram negative bacteria, TLR-5 agonists, fragments of flagellins capable of binding to TLR-5 receptors, saponins, analogues of saponins, QS-21, purified saponin fractions, ISCOMS and saponin combinations with sterols and lipids.

In yet another embodiment, the disclosure provides a method of controlling particle size in an adjuvant-bound dried vaccine composition, the method comprising: combining at least one aluminum-salt adjuvant, at least one buffer system, at least one glass-forming agent, and at least one antigen to create a liquid vaccine formulation; freezing the liquid vaccine formulation to create a frozen vaccine formulation; and lyophilizing the frozen vaccine formulation to create a dried vaccine composition, wherein following dilution of the dried vaccine composition with an aqueous diluent to form a reconstituted vaccine composition the mean particle diameter of the reconstituted vaccine composition is less than 100 micrometers. In another aspect, the at least one aluminum-salt adjuvant is selected from the group consisting of aluminum hydroxide, aluminum phosphate and aluminum sulfate. In a further aspect, the aluminum-salt adjuvant is aluminum hydroxide. In another aspect, the at least one buffer system is selected from the group consisting of acetate, succinate, citrate, prolamine, histidine, borate, carbonate and phosphate buffer systems. In a further aspect, the at least one buffer system is selected from succinate and phosphate buffer systems. In one aspect, the at least one glass-forming agent is selected from the group consisting of trehelose, sucrose, ficoll, dextran, sucrose, maltotriose, lactose, mannitol, hydroxyethyl starch, glycine, cyclodextrin, povidone, and potassium salts. In a specific aspect, the glass-forming agent is trehalose. In a further specific aspect, the glass-forming agent trehalose is present in a weight to volume concentration of from about 5% to about 20% in the liquid vaccine formulation. In another aspect, the glass-forming agent trehalose is present in a weight to volume concentration of from about 7% to about 15% in the liquid vaccine formulation. In one aspect, the freezing step comprises one of tray freezing, shelf freezing, spray-freezing and shell-freezing. In another aspect, the freezing step comprises spray-freezing. In a further aspect, the mean particle diameter of the reconstituted vaccine composition is less than 6 micrometers. In one aspect, the concentration of the glass forming agent in the selecting step is decreased as the rate of cooling the liquid vaccine formulation to a frozen state in the cooling step is increased.

In an alternative embodiment, the disclosure provides an adjuvant composition for use in a dried vaccine composition, the adjuvant composition comprising: an aluminum-salt adjuvant, a glass-forming agent, and a buffer salt. In one aspect, the aluminum-salt adjuvant is selected from aluminum hydroxide and aluminum phosphate. In another aspect, the glass-forming agent is trehalose. In a further aspect, the buffer salt is selected from one or more of the group consisting of sodium succinate, potassium succinate, sodium phosphate and potassium phosphate.

In yet another embodiment, the disclosure provides an adjuvant-bound dried vaccine composition having limited mean particle diameter, the composition produced by a method comprising: blending at least one adjuvant, at least one glass forming agent, and at least one antigen in a buffer system to create a liquid vaccine formulation; cooling the liquid vaccine formulation rapidly to a frozen state to create a frozen vaccine formulation; and lyophilizing the frozen vaccine formulation to create a dried vaccine composition, wherein following dilution of the dried vaccine composition with an aqueous diluent to form a reconstituted vaccine composition, the mean particle diameter of the reconstituted vaccine composition is less than 100 micrometers.

In another embodiment, the disclosure provides a method of controlling particle size in a frozen vaccine formulation, the method comprising: combining at least one aluminum-salt adjuvant, at least one buffer system, at least one glass-forming agent, and at least one antigen to create a liquid vaccine formulation; freezing the liquid vaccine formulation to create a frozen vaccine formulation; and lyophilizing the frozen vaccine formulation to create a dried vaccine composition, wherein following thawing and dilution of the dried vaccine composition with an aqueous diluent to form a reconstituted vaccine composition the mean particle diameter of the reconstituted vaccine composition is less than 100 micrometers. In one aspect, the at least one aluminum-salt adjuvant is selected from the group consisting of aluminum hydroxide, aluminum phosphate and aluminum sulfate. In another aspect, the aluminum-salt adjuvant is aluminum hydroxide. In a further aspect, the at least one buffer system is selected from the group consisting of acetate, succinate, citrate, prolamine, histidine, borate, carbonate and phosphate buffer systems. In one aspect, the at least one buffer system is selected from succinate and phosphate buffer systems. In another aspect, the at least one glass-forming agent is selected from the group consisting of trehalose, sucrose, ficoll, dextran, sucrose, maltotriose, lactose, mannitol, hydroxyethyl starch, glycine, cyclodextrin, povidone, and potassium salts. In a specific aspect, the glass-forming agent is trehalose. In a further specific aspect, the glass-forming agent trehalose is present in a weight to volume concentration of from about 5% to about 20% in the liquid vaccine formulation. In another specific aspect, the glass-forming agent trehalose is present in a weight to volume concentration of from about 7% to about 15% in the liquid vaccine formulation. In one aspect, the freezing step comprises one of tray freezing, shelf freezing, spray-freezing and shell-freezing. In another aspect, the freezing step comprises spray-freezing. In a further aspect, the mean particle diameter of the reconstituted vaccine composition is less than 6 micrometers.

In another aspect, the liquid vaccine formulation is prepared as a hypertonic mixture prior to freezing, wherein upon dilution of the dried vaccine composition with an aqueous diluent to form a reconstituted vaccine composition, the tonicity of the reconstituted vaccine composition is adjusted to isotonic levels. In yet another aspect, a formulation is prepared wherein the volatile salt is removed by lyophilization, yielding, upon reconstitution, a vaccine preparation with tonicity reduced relative to the starting formulation while retaining the same concentration of antigens and adjuvants.

BRIEF DESCRIPTION OF THE DRAWINGS

Figure 2:
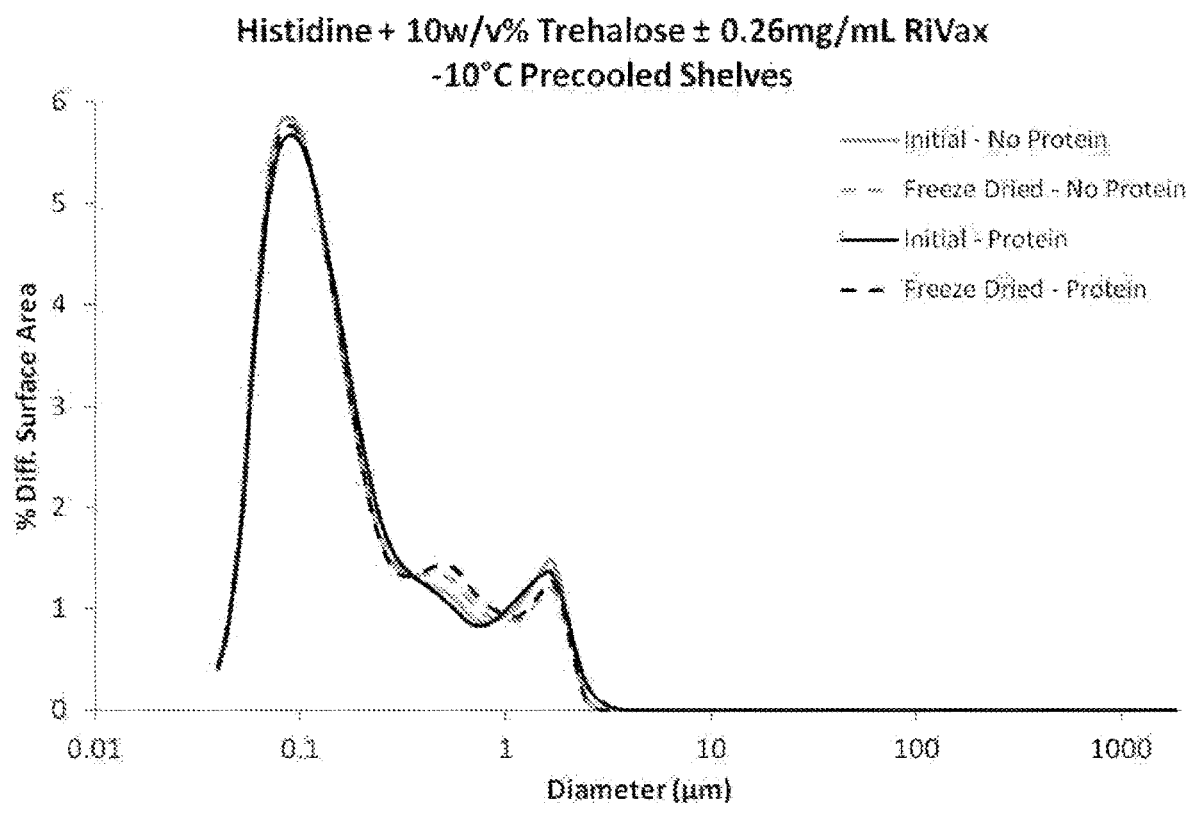

FIG. 2 depicts particle size distributions of histidine formulations based on % surface area before and after freeze drying.

Figure 3:
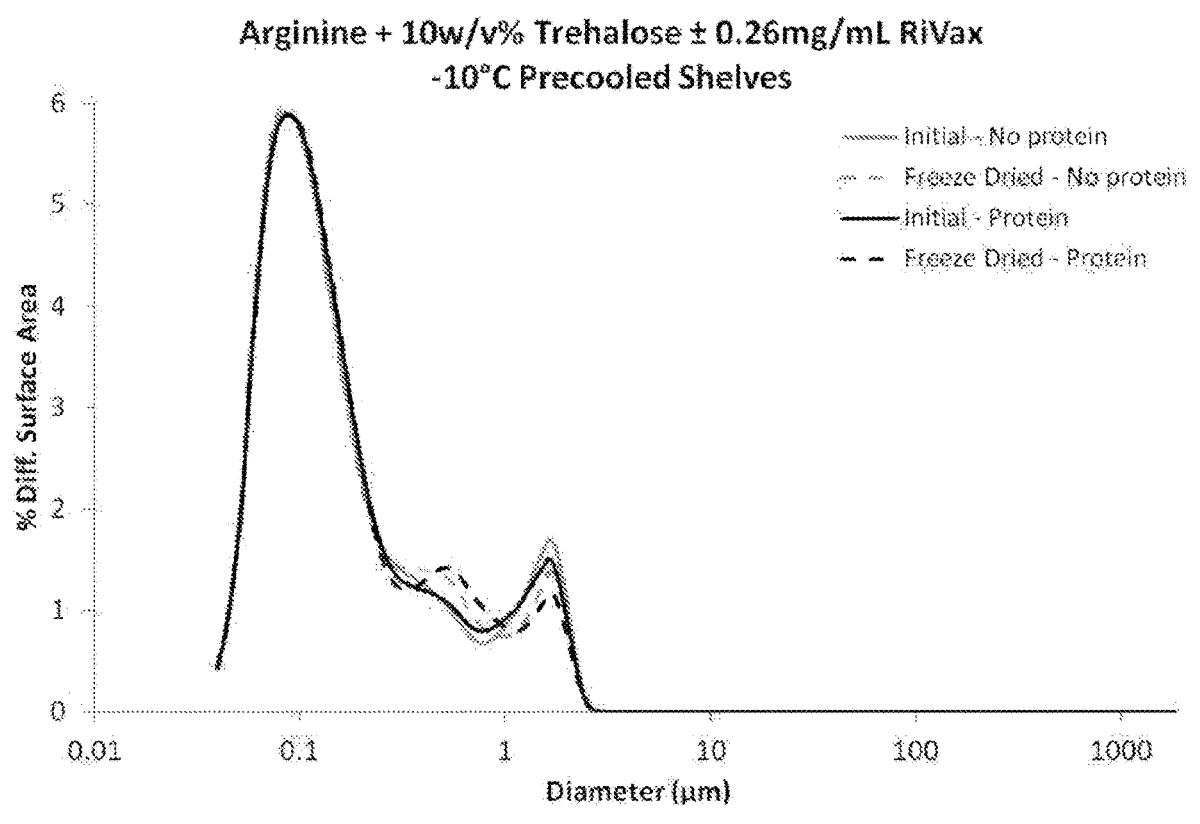

FIG. 3 depicts particle size distributions of arginine formulations based on % surface area before and after freeze drying.

FIGS. 10(A)-10(D) show particle size distributions before and after freeze drying cycles under four conditions and increasing concentrations of trehalose. Faster rates of freezing before primary and secondary drying and higher concentrations of trehalose result in particle size distributions after freeze drying most similar to the initial particle distribution. From slowest to fastest: room temperature tray (A), −10° C. Pre-cooled Tray (B), Liquid Nitrogen dip (C), Liquid Nitrogen spray Freeze Drying (D). Formulation consisted of 1 mg/ml as Alhydrogel, 10 mM histidine, pH 6.0, with 0-12% trehalose.

FIG. 14 shows the results of vaccination of a liquid RTA vaccine adsorbed to Alhydrogel in which various dose of RTA were used to vaccinate groups of 8 Swiss Webster mice. When the vaccine was stored at 40° C. for 1 month prior to vaccination, none of the animals exposed to ricin toxin survived and a significant loss of immunogenicity was observed. The vaccine stored at 4° C. for one month induced total protection at the highest doses and partial protection in mice at lower doses.

FIG. 16 shows endpoint titer data from immunized mice. Endpoint Titers=reciprocal endpoint anti-RTA titers. Neutralizing IC50 Titers=the dilution of sera required to protect 50% of the cells in a well from ricin cytotoxicity Not shown here, but none of the sham immunized mice (#1-10 (except 5) had any anti-RTA titers in their sera. #1 sham immunized mouse sera was also tested for neutralizing capacity in vitro, and did not protect cells.

FIG. 17 shows total and neutralizing titers obtained from individual sera post 2nd vaccination of Swiss Webster mice with adsorbed liquid vaccine prior to lyophilization.

DETAILED DESCRIPTION OF THE INVENTION

Definitions

Figure 1:
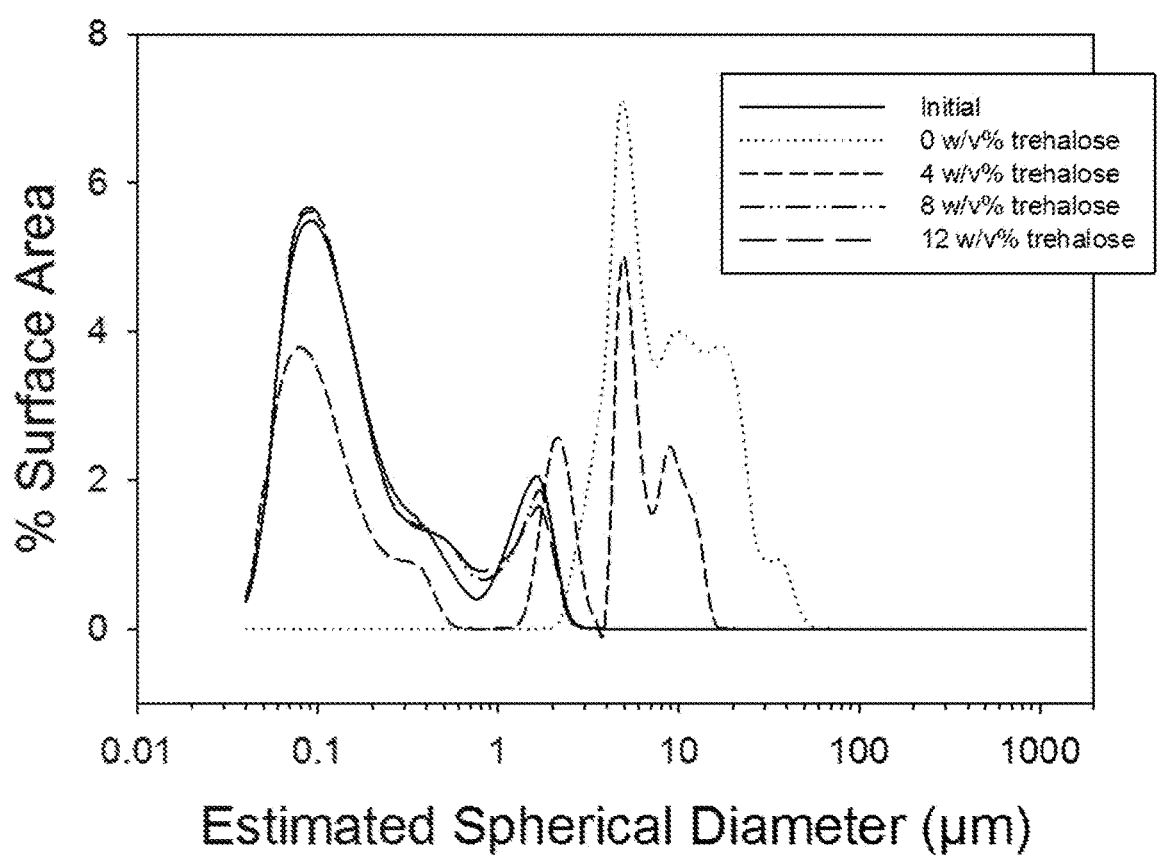
FIG. 1 depicts particle size distributions before and after freeze drying and reconstitutions based on % surface area.
Figure 4:
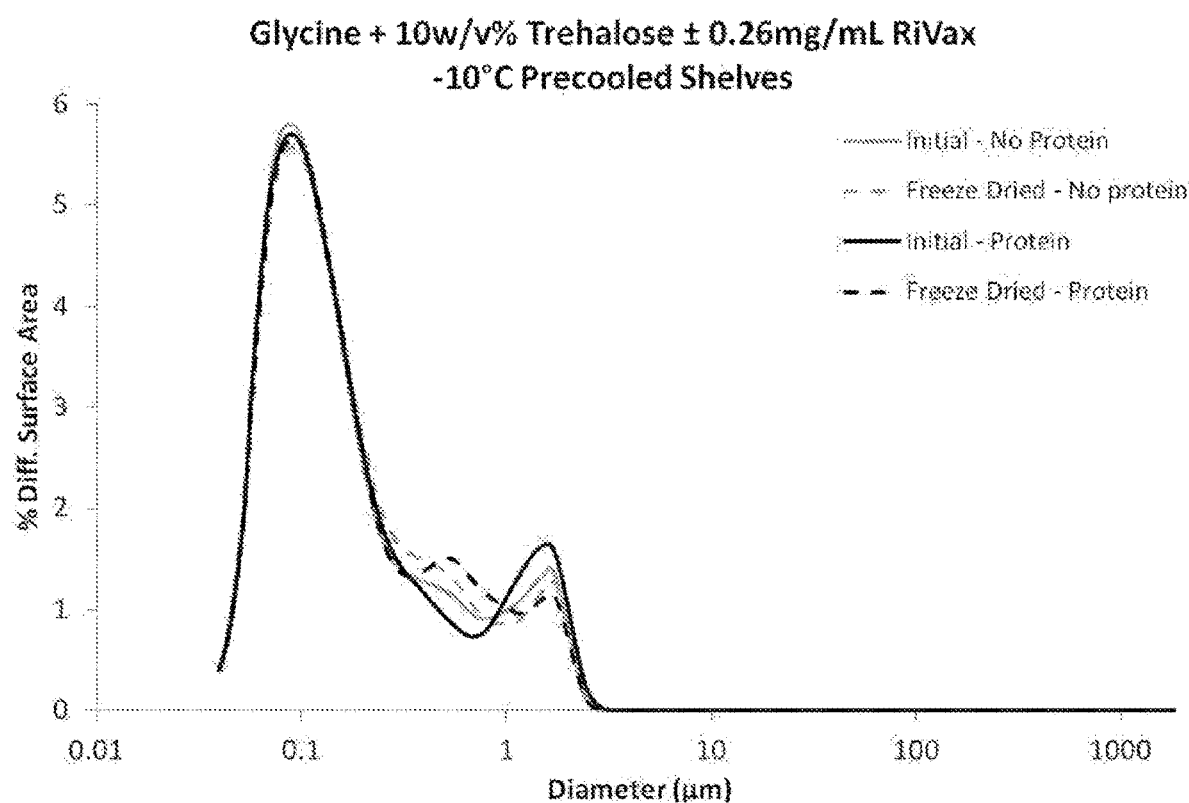
FIG. 4 depicts particle size distributions of glycine formulations based on % surface area before and after freeze drying.
Figure 5A:
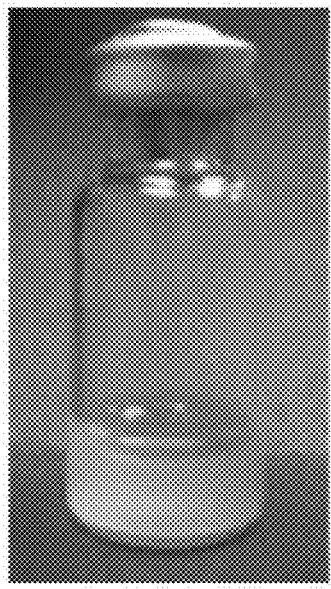
FIGS. 5(a)-5-(c) show Alhydrogel particles settling over time in 10 mM histidine buffer pH 6. (a) No settling; (b) After 30 minutes of settling; and (c) After 3 hours of settling.
Figure 5B:
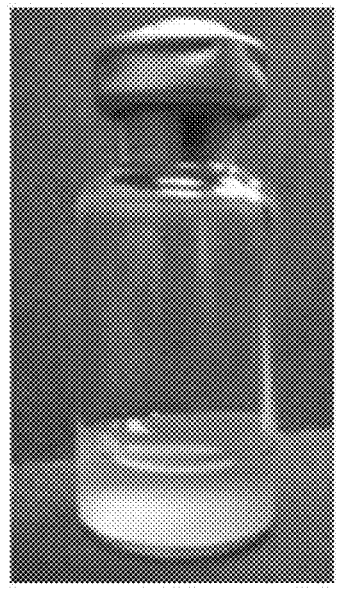
Figure 5C:
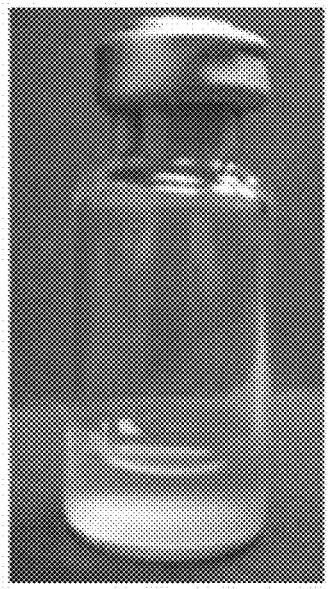

Trehalose dehydrate (high purity, low endotoxin) was obtained from Ferro Pfanstiehl (Cleveland, Ohio). Arginine, glycine, histidine, sodium citrate, and ammonium acetate were purchased from Sigma Chemical Company (St. Louis, Mo.). Alhydrogel™ 2.0% (aluminum hydroxide adjuvant), made by Brenntag Biosector, was purchased through E.M. Sergeant Pulp & Chemical Co, Inc (Clifton, N.J.). 3-ml and 5-ml lyophilization vials and caps were obtained from West Pharmaceutical Services.

Sample Preparation

Aqueous solutions were prepared containing different concentrations of trehalose (0-15 w/v %). Unless otherwise noted, samples were prepared in 10 mM buffer (as indicated) at pH 6.0 and contained 1 mg/ml Al (as Alhydrogel™). Samples were processed as one-ml aliquots. With the exception of the adjuvant, all aqueous solutions were passed through a 0.2 µm filter prior to formulation.

Surface Charge Zeta Potential

Zeta potentials were measured for suspensions of aluminum hydroxide (Alhydrogel) in various formulations to probe electrostatic interactions. Formulations without antigen were then prepared to determine if aggregation of particles occurred during freeze drying. Alhydrogel at a concentration of 1 mg Al/mL was combined in 10 mM buffer (glycine, arginine, histidine, ammonium acetate, sodium citrate) at pH 6 with the stabilizer trehalose ranging from 0-12 w/v %. To determine if the rate of freezing affects particle aggregation, formulations were freeze dried using four methods of freezing: Room Temperature Tray Freezing, −10° C. Pre-cooled Tray Freezing, Liquid Nitrogen Dip Freezing, and Liquid Nitrogen Spray Freezing before primary and secondary drying. Protein was also added to formulations to see its effect on particle size after freeze drying and reconstitution. Particle size distributions in the range of 0.04-2000 µm were characterized by laser diffraction for each formulation.

Lyophilization

An FTS Systems Lyostar lyophilizer was used for the freeze-drying of samples. Samples were frozen at various cooling rates as follows from slowest to fastest: (i) Vials prepared at room temperature were placed on the lyophilizer trays and kept at room temperature for 1 hour prior to iniating the (ii.) Frozen by placing the samples in lyophilizer, equilibrating 1 hr at a shelf temperature of −10° C., then cooling the shelves at 0.5° C./min to −40° C. ("−10 pre-cooled tray-freezing"); (ii.) Frozen by immersion of bottom of vial into liquid $N_2$ (LN2 Dip Freeze Drying); and (iii.) Spray-freezing by dropping by ~20 µl droplets into liquid $N_2$. (LN2 spray freeze drying). Tray-frozen and liquid $N_2$-immersed samples were processed in 3-ml lyophilization vials, while the spray-frozen samples were processed in 5-ml lyophilization vials. Vials containing samples frozen using liquid $N_2$ were quickly transferred to the lyophilizer placed on lyophilizer shelves pre-cooled to −40° C. Samples were spaced in the lyophilizer so that they were each separated from one another and were encircled with a row of vials containing water.

Primary drying of the samples was achieved by setting the shelf temperature to −20° C. and applying vacuum at 60 mTorr for 20 hours, and was followed by secondary drying, in which shelf temperatures were ramped from −20° C. to 0° C. at 0.2° C./min, to 30° C. at 0.5° C./min and finally held at 30° C. for 5 hours. Samples were sealed under vacuum and reconstituted with DI water prior to analysis. The variations of the freezing and drying cycles are depicted in (FIGS. 10(a)-10(D)).

Particle Size Distributions

Particle size distributions (PSD) were measured using a Beckman-Coulter LS230 laser diffraction particle size analyzer. Three one-ml samples were required for each run, and three replicates of each run were completed per formulation. Reported PSD's are surface area weighted and are composites of three runs.

EXAMPLES

I. −10° C. Pre-Cooled Tray Freeze Drying with Varying Settling Time of Particles 10 mM histidine buffer at pH 6.0, 1 mg/mL Al from Alhydrogel, and 0, 4, 8 or 12 w/v % trehalose was combined and rotated end over end for 30 minutes at 4° C. 1 mL of the solution was placed in each 3 mL glass freeze drying vial. The formulations were placed on −10° C. pre-cooled shelves in the freeze drier and freeze dried as follows in the table below. Following freeze drying, the chamber was backfilled with dry nitrogen gas and the vials were sealed.

TABLE 1

| Stage | Time for Step | Initial Temp (° C.) | Final Temp (° C.) | Pressure | Rate |
|---|---|---|---|---|---|
| Freezing | 0.25 hours | −10 | −10 | Atmospheric | Constant temp −10 |
|  | 1 hours | −10 | −40 | Atmospheric | −0.5° C./min |
|  | 1 hour | −40 | −40 | Atmospheric | Constant temp −40 |
| Primary Drying | 0.5 hours | −40 | −40 | 60 mTorr | Constant temp −40 |
|  | 0.5 hour | −40 | −20 | 60 mTorr | Increase temp |
|  | 20 hours | −20 | −20 | 60 mTorr | Constant temp −20 |
| Secondary Drying | 1 hour 40 min | −20 | 0 | 60 mTorr | 0.2° C./min |
|  | 1 hour | 0 | 30 | 60 mTorr | 0.5° C./min |
|  | 5 hours | 30 | 30 | 60 mTorr | Constant temp 30 |

Particle Size Analysis

Particle size analysis was done on the solutions before they were freeze dried as well as on the freeze dried samples reconstituted in 1 mL of DI water. Laser diffraction particle size analysis was done using a LS 230 instrument made by Beckman. For the analysis no sonication was done on the sample chamber. The model used for calculating particle size distributions used a solution refractive index of 1.33 and a sample refractive index of 1.57. Approximately 6 mL of sample was required to be added to filtered DI water in the analyzer before the reading was taken. For each run three ninety second averaged particle size distributions were taken. For each formulation three runs were taken.

Results

When formulations contained higher concentrations of trehalose (8-12 w/v %) the initial particle size distribution was able to be maintained as seen in FIG. 1.

II. −10° C. Pre-Cooled Tray Freeze Drying 10 mM buffer, 1 mg/mL Al from alhydrogel, 10 w/v % trehalose with and without 0.26 mg/mL rRTA was combined and rotated end over end for 30 minutes at 4° C. 1 mL of the solution was placed in each 3 mL glass freeze drying vial. The formulations were placed on −10° C. pre-cooled shelves in the freeze drier and freeze dried as follows in the table below. Following freeze drying, the chamber was backfilled with dry nitrogen gas and the vials were sealed.

TABLE 2

| Stage | Time for Step | Initial Temp (° C.) | Final Temp (° C.) | Pressure | Rate |
|---|---|---|---|---|---|
| Freezing | 0.25 hours | −10 | −10 | Atmospheric | Const. temp 5 |
|  | 1 hours | −10 | −40 | Atmospheric | −0.5° C./min |
|  | 1 hour | −40 | −40 | Atmospheric | Const. temp −40 |
| Primary Drying | 0.5 hours | −40 | −40 | 60 mTorr | Const. temp −40 |
|  | 0.5 hour | −40 | −20 | 60 mTorr | Increase temp |
|  | 20 hours | −20 | −20 | 60 mTorr | Const. temp −20 |
| Secondary Drying | 1 hour 40 min | −20 | 0 | 60 mTorr | 0.2° C./min |
|  | 1 hour | 0 | 30 | 60 mTorr | 0.5° C./min |
|  | 5 hours | 30 | 30 | 60 mTorr | Const. temp 30 |

Particle Size Analysis

Particle size analysis was done on the solutions before they were freeze dried as well as on the freeze dried samples reconstituted in 1 mL of DI water. Laser diffraction particle size analysis was done using a LS 230 instrument made by Beckman. For the analysis no sonication was done on the sample chamber. The model used for calculating particle size distributions used a solution refractive index of 1.33 and a sample refractive index of 1.57. Approximately 6-7 mL of sample was required to be added to filtered DI water in the analyzer before the reading was taken. For each run three ninety second averaged particle size distributions were taken. For each formulation three runs were taken.

Results

Figure 6:
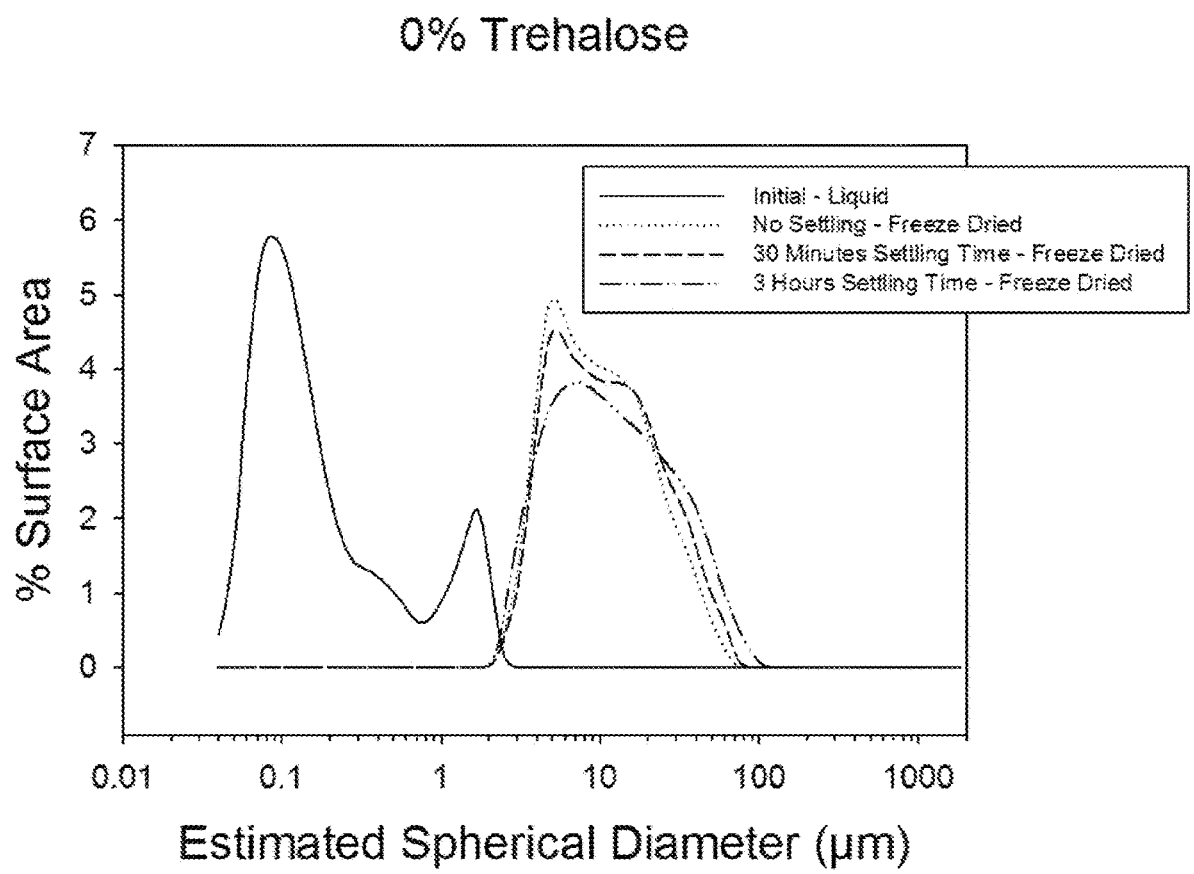
FIG. 6 depicts particle size distributions based on surface area after allowing particles to settle for varying amounts of time before freeze drying with −10° C. pre-cooled shelves. Samples contained 1 mg/mL Al in 10 mM histidine buffer at pH 6.

In arginine, histidine, and glycine buffers containing 10 w/v % trehalose, both with and without rRTA protein present, the particle size distribution was able to be maintained before freeze drying and after using −10° C. pre-cooled shelves before freeze drying. Particle size distributions can be seen in FIGS. 1-3. Particle size distributions could possibly be maintain better with pre-cooled shelves before freeze drying than tray freeze drying because the adjuvant particles have less time to settle before the formulation freezes when pre-cooled shelves are used.

III. −10° C. Pre-Cooled Tray Freeze Drying with Varying Settling Time of Particles at 3 Hour, 30 Minute and 0 Timepoints Before Freeze Drying 10 mM histidine buffer at pH 6, 1 mg/mL Al from alhydrogel, and 0 or 8 w/v % trehalose was combined and rotated end over end for 30 minutes at 4° C. 1 mL of the solution was placed in each 3 mL glass freeze drying vial. The vials were divided into three groups that were allowed to rest for 3 hours, 30 minutes and 0 minutes before being placed in the freeze drier. Once vials were filled they were allowed to sit at 4° C. until it was time to be loaded in the freeze drier. The formulations were placed on −10° C. pre-cooled shelves in the freeze drier and freeze dried as follows in the table below. Following freeze drying, the chamber was backfilled with dry nitrogen gas and the vials were sealed.

TABLE 3

| Stage | Time for Step | Initial Temp (° C.) | Final Temp (° C.) | Pressure | Rate |
|---|---|---|---|---|---|
| Freezing | 0.25 hours | −10 | −10 | Atmospheric | Constant temp 5 |
| | 1 hours | −10 | −40 | Atmospheric | −0.5° C./min |
| | 1 hour | −40 | −40 | Atmospheric | Constant temp −40 |
| Primary Drying | 0.5 hours | −40 | −40 | 60 mTorr | Constant temp −40 |
| | 0.5 hour | −40 | −20 | 60 mTorr | Increase temp |
| | 20 hours | −20 | −20 | 60 mTorr | Constant temp −20 |
| Secondary Drying | 1 hour 40 min | −20 | 0 | 60 mTorr | 0.2° C./min |
| | 1 hour | 0 | 30 | 60 mTorr | 0.5° C./min |
| | 5 hours | 30 | 30 | 60 mTorr | Constant temp 30 |

Particle Size Analysis

Particle size analysis was done on the solutions before they were freeze dried as well as on the freeze dried samples reconstituted in 1 mL of DI water. Laser diffraction particle size analysis was done using a LS 230 instrument made by Beckman. For the analysis no sonication was done on the sample chamber. The model used for calculating particle size distributions used a solution refractive index of 1.33 and a sample refractive index of 1.57. Approximately 6 mL of sample was required to be added to filtered DI water in the analyzer before the reading was taken. For each run three ninety second averaged particle size distributions were taken. For each formulation two runs were taken.

Results

Before samples were placed in the freeze drier they were allowed to settle for 0 minutes, 30 minutes or 3 hours. In FIGS. 5(*a*)-5(*c*), a vial containing 1 mg/mL Al from Alhydrogel in 10 mM histidine is shown at various time points during settling. Without settling, the formulation appears to be cloudy throughout the solution (FIG. 5*a*). After 30 minutes of settling the majority of the alhydrogel particles appear to be close to the bottom of the vial with a slightly cloudy solution above (FIG. 5*b*). After 3 hours of settling the alhydrogel particles have settled closer to the bottom of the vial and leave a clear solution above the alhydrogel layer (FIG. 5*c*).

When the formulation contained alhydrogel and histidine without trehalose, the particle size distribution was shifted towards larger particles from the initial particle size distribution (FIG. 6). Formulations that were allowed to settle for less time produced slightly smaller particles than those allowed to settle for longer periods of time.

Figure 7:
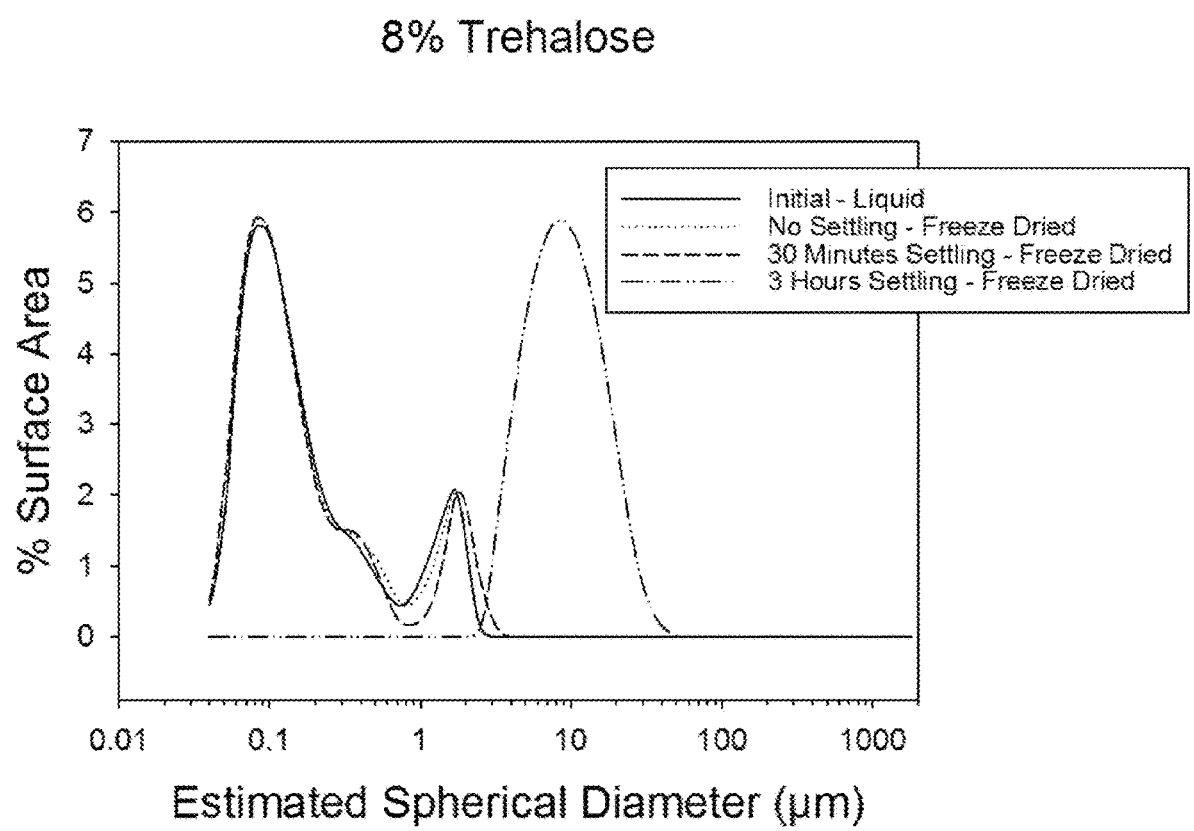
FIG. 7 depicts particle size distributions based on surface area after allowing particles to settle for varying amounts of time before freeze drying with −10° C. pre-cooled shelves. Samples contained 1 mg/mL Al and 8 w/v % trehalose in 10 mM histidine buffer at pH 6.

When formulations contained 8 w/v % trehalose, the amount of time the samples were allowed to settle before being placed in the freeze drier effected the particle size distribution (FIG. 7). When the formulation was not allowed to settle before being placed in the freeze drier, the particle size distribution was very similar to the initial particle size distribution before freeze drying. After 30 minutes of settling the particle size distribution starts to shift to larger particle sizes and at 3 hours of settling the particles are significantly larger than the initial particle size distribution.

Figure 8:
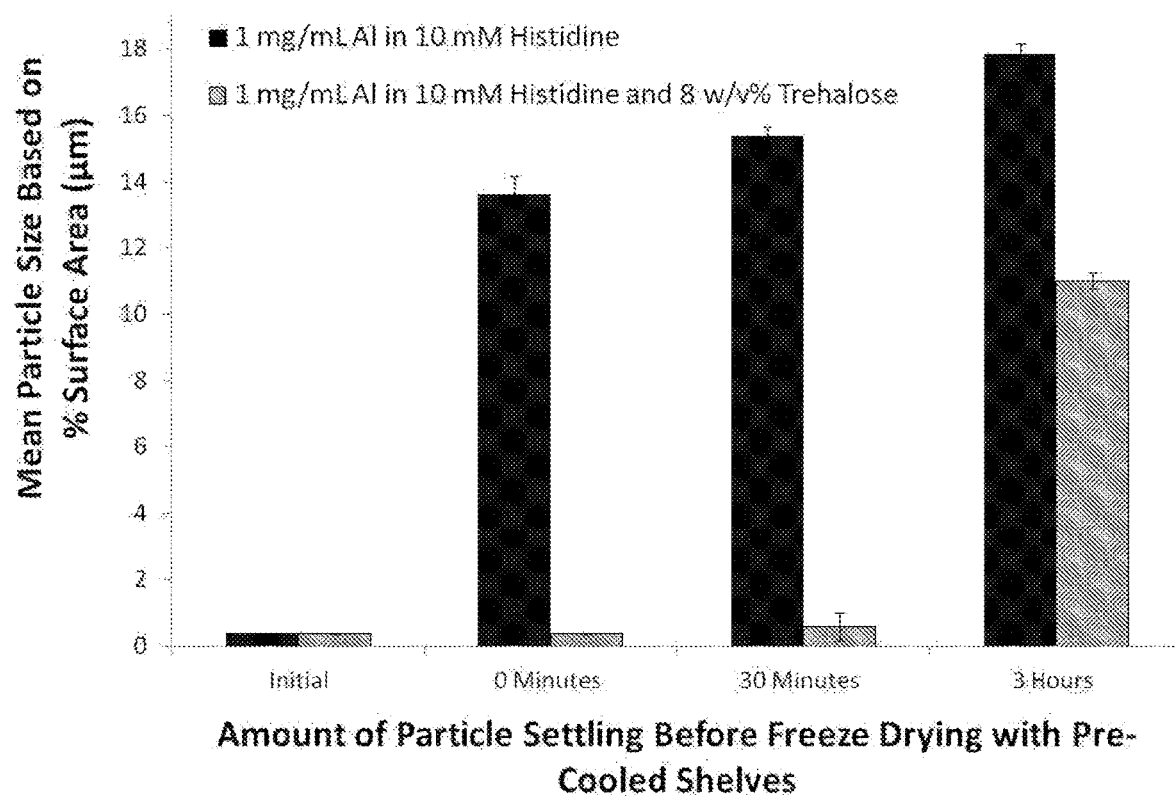
FIG. 8 shows a comparison of mean particle size between formulations of 1 mg/mL Al in 10 mM histidine with and without trehalose while varying the settling time before freeze drying.
Figure 9:
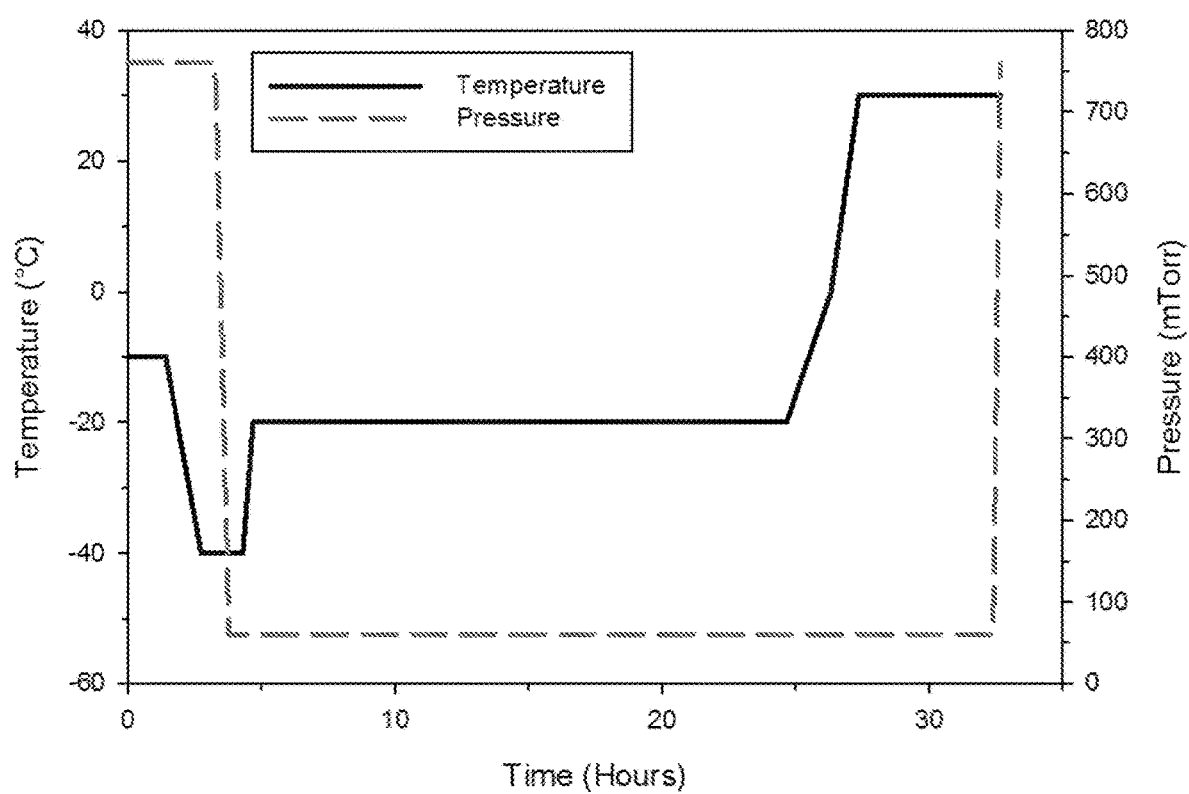
FIG. 9 demonstrates the steps during lyophilization in which 1 ml vaccine samples contained in 3 ml glass vials were treated to varying freezing rates with an FTS System LyoStar Freeze Drying System before primary and secondary freezing. After freeze drying, vials were purged with nitrogen gas sealed and stored at −80° C. before further analysis.

When comparing the formulations with trehalose in comparison the ones without trehalose, trehalose presence in the formulation in maintains the particle size distribution after the freeze drying process. Although the initial mean particle size before freeze drying is the same with and without trehalose present in the formulation, the mean particle size after freeze drying is smaller when trehalose is present in the formulation at each amount of settling before freeze drying as can be seen in FIG. 8. From these experiments we can also see the importance of not allowing the samples to settle before loading in the freeze drier if it is desired to maintain the initial particle size.

IV. Immunogenicity of Ricin Vaccine Subunit in Experimental Animals.

Figure 11:
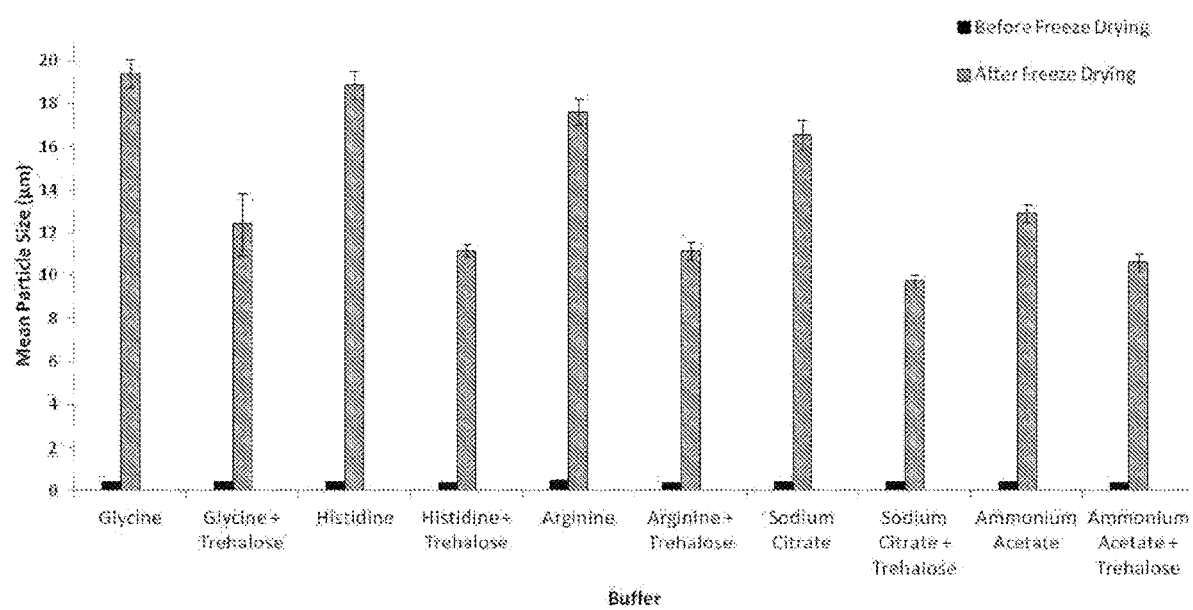
FIG. 11 shows the dependence of particle size distribution after freeze drying of room temperature freeze drying. Room temperature freeze drying was carried out as in FIG. 10(A). With room temperature incubation on trays prior to the freezing cycle, particle size distribution shifted from <1 micron to >than 20 microns, and the presence of 8% trehalose reduce the magnitude of the particle size shift.
Figure 12:
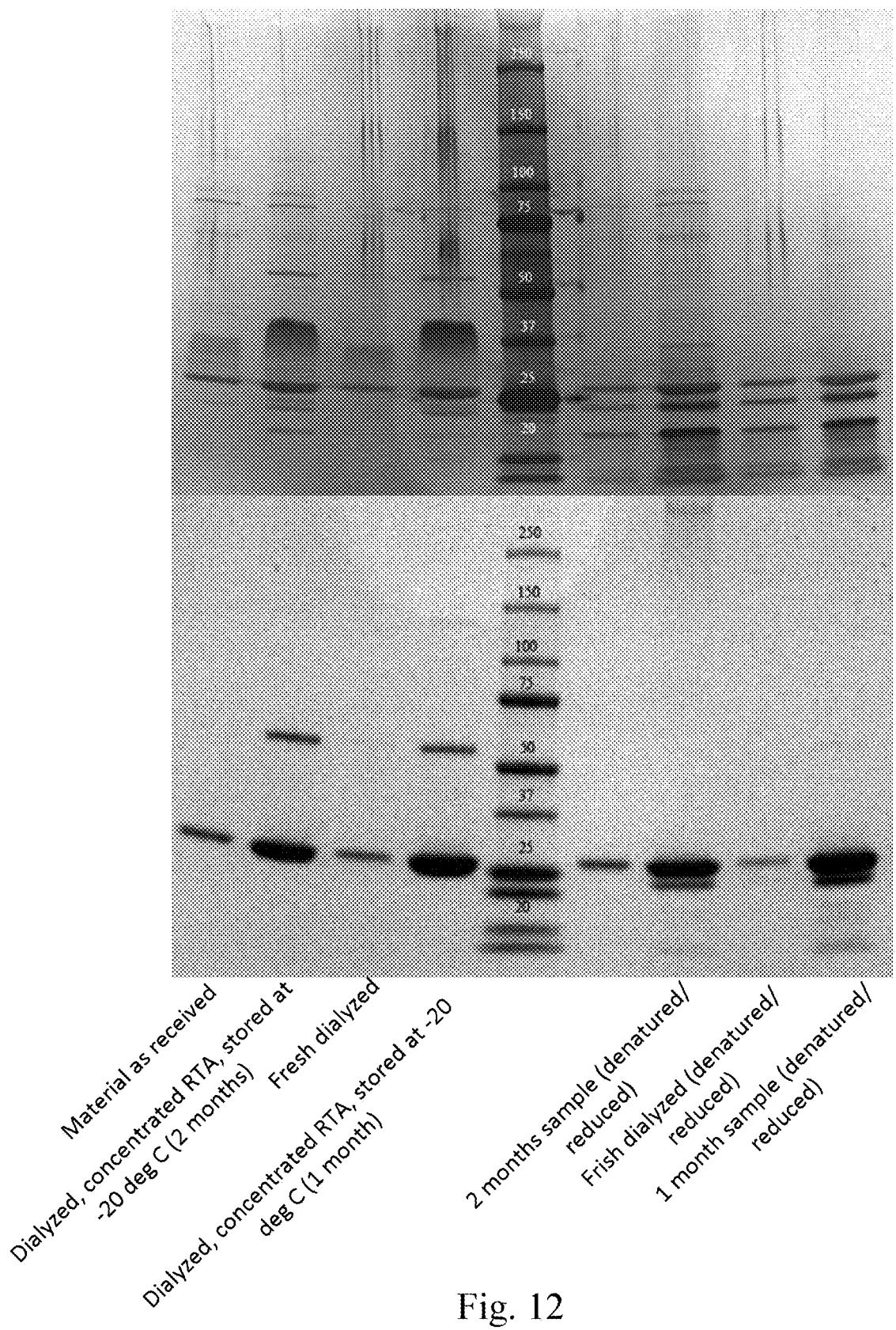
FIG. 12 shows SDS PAGE of RTA dissolved in 10 mM histidine, pH 6.0, 144 mM NaCl with 50% w/v glycerol in comparison to RTA dialyzed, concentrated and stored at −20 degree C. (Top panel—silver stain, bottom panel—Coomassie stain. The same set of samples was used to perform both studies).
Figure 13:
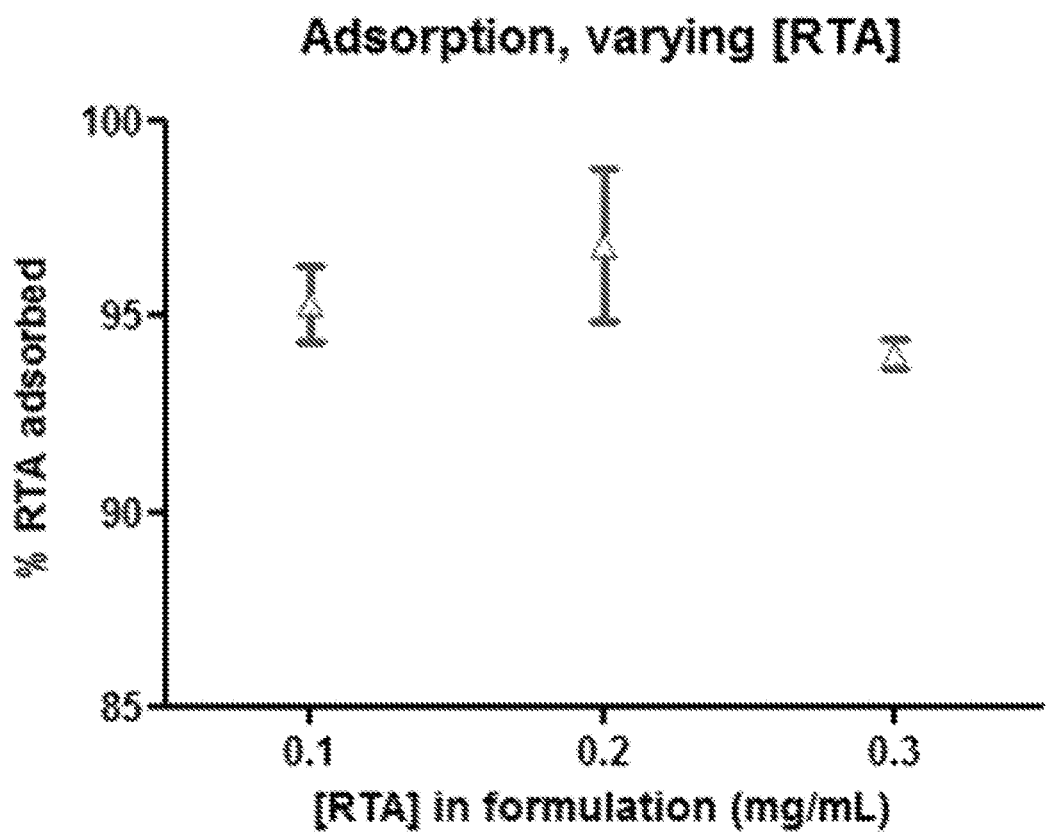
FIG. 13 shows adsorption of RTA to Alhydrogel prior to lyophilizaiont. The concentration of RTA was varied keeping the concentration of Al at 1 mg/mL. At least 95% of the RTA protein was adsorbed to the surface of Alhydrogel at pH 6.0.
Figure 14:
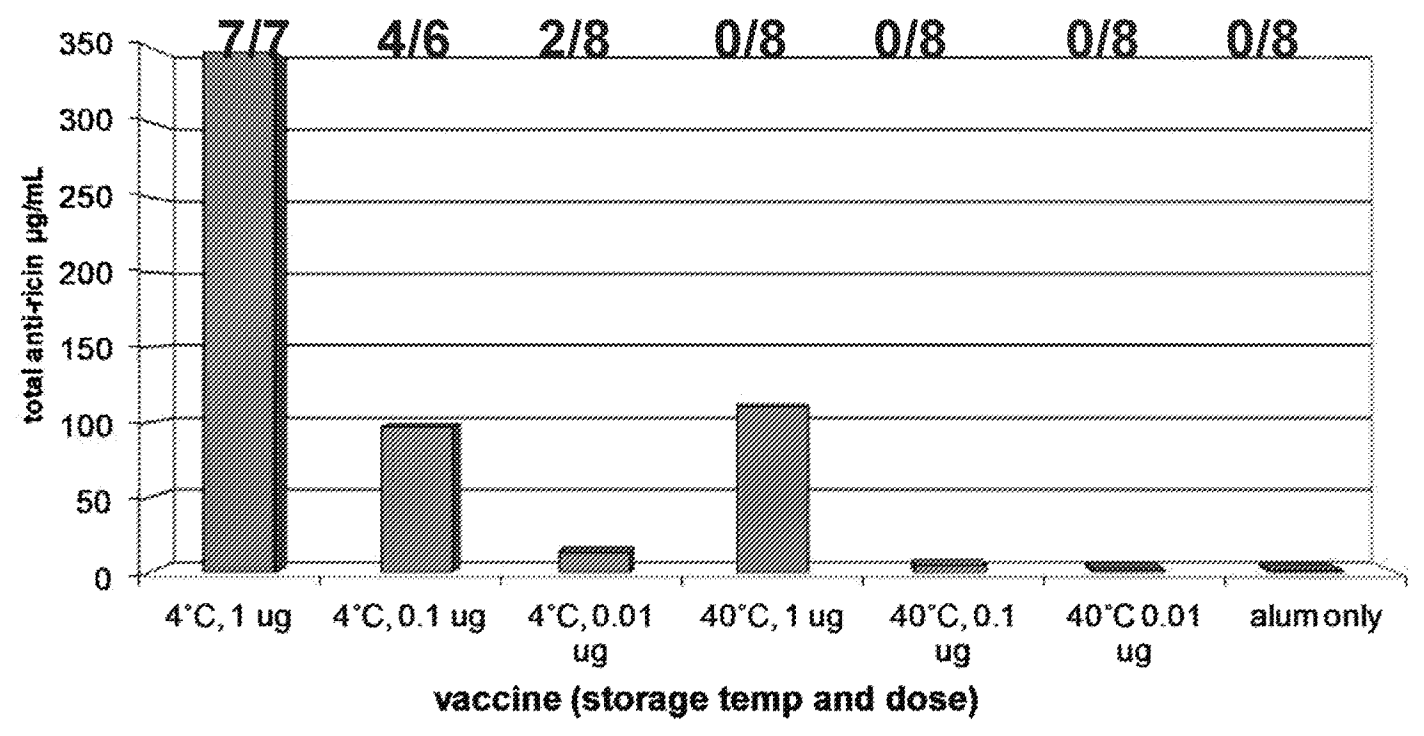

As an example, a thermostable lyophilized ricin subunit vaccine was constructed and tested. Ricin A chain vaccine was used because it is subject to aggregation and denaturation in aqueous buffers and is prone to losses in structural integrity that affect immunogenicity and the induction of neutralizing antibodies involved in protection against ricin toxin exposure. A lyophilized ricin vaccine was prepared as follows. RTA dissolved in glycerol was dialyzed against 10 mM histidine buffer, pH 6.0 to remove glycerol (FIG. 11). The liquid suspension vaccine was placed into vials and subjected to lyophilization as described in FIGS. 10(A)-10(D) to compare precooled freeze drying at −10 degrees C. with vaccine at room temperature prior to initiating of the primary freeze drying cycle at −40° C. The dried vaccines were stored either at refrigeration temperature (4-8° C.) or at elevated temperature (40-60° C.). Samples from the stored lyophilized vaccine were withdrawn periodically and tested for structural integrity by assessment of binding of a diagnostic monoclonal antibody termed R70 (Neal, O'Hara et al., 2010, A monoclonal immunoglobulin G antibody directed against an immunodominant linear epitope on the ricin A chain confers systemic and mucosal immunity to ricin, Infect Immun, 78:552-61). In addition, vaccines were subjected to additional biophysical tests including the determination of intrinsic fluorescence diagnostic of tertiary structure of protein bound to aluminum, determination of residual water, and immunogenicity/potency in mice. Immunogenicity was determined by injecting Swiss Webster mice as below and determining total antibodies against the vaccine by ELISA and determination of ricin neutralizing antibodies. Mice were exposed to ricin toxin at day 35 by injection of 10×LD50 dose of toxin and lethality was determined in the exposed animals. In addition, peptide scans were performed in which serum from vaccinated and control mice were assessed for response to overlapping peptides encompassing the RTA molecule. This was done to determine the immunodominant regions and their preservation during high and low temperature storage conditions. When control liquid vaccine was used to vaccinate mice 3× by intramuscular injection, incubation of the vaccine at 40° C. for one month resulted in loss of immunogenicity and the ability to induce protective immunity (FIG. 14).

During the study, each Swiss Webster mouse was bled three times and injected with a vaccine formulation twice. Before the initial injection mice were bled and then on day 0 injected with a vaccine formulation. The initial bleeding was necessary so that each mouse could be its own baseline. 21 days later the mice were bled and injected with a booster vaccine formulation. 35 days after the initial injection the mice were bled one last time. Before bleeding procedures the mice were anesthetized using is isofluorane inhalant. Blood was drawn from the retro-orbital venous sinus of the mice. A drop of proparacaine was put on the eye from which blood was drawn and then blood was collected using 504, capillary tubes. Approximately 100-2004, of blood was drawn during each bleeding.

TABLE 4

| Group | Contents |
| --- | --- |
| Negative Control | Freeze dried Alhydrogel in histidine buffer |
| Negative Control | Freeze dried Alhydrogel in ammonium acetate buffer |
| Positive Control | Liquid formulation of rRTA and Alhydrogel |
| Experimental Group 1 | Freeze dried (Room temp shelves) rRTA and Alhydrogel in histidine buffer |
| Experimental Group 2 | Freeze dried (Room temp shelves) rRTA and Alhydrogel in ammonium acetate buffer |
| Experimental Group 3 | Freeze dried (Pre-cooled shelves) rRTA and Alhydrogel in histidine buffer |
| Experimental Group 4 | Freeze dried (Pre-cooled shelves) rRTA and Alhydrogel in ammonium acetate buffer |

To create variations in the formulation particle size, different buffers such as histidine and ammonium acetate and the variation of freezing rate before freeze drying (such as room temperature shelves or pre-cooled shelves before freeze drying) were used. All samples contained the disaccharide trehalose up to 15% (w/V) and Alhydrogel is an aluminum hydroxide vaccine adjuvant used at 0.85-1 mg/ml total aluminum.

V. Controlled Lyophilization of Adsorbed Ricin Vaccine.

The central objective of this invention is to make subunit vaccines by employing controlled lyophilization of protein, aluminum adjuvant, and immunostimulant components for reconstitution with water at the point of use. Using aluminum adjuvant, it has not been feasible or possible up to this point to adequately combine these components together without loss of vaccine effectiveness on the one hand and gross clumping and inability to rehydrate adequately. A number of different conditions for precisely controlling points in the lyophilization cycle examining a spectrum of buffer conditions, salt conditions, and lyophilization cycle conditions and have reported that we had been able to define conditions for retaining gross integrity including protein structure pre and post lyophilization.

VI. Generation of Prototype Freeze Dried Vaccines.

A series of freeze dried formulation was made according to the general lyophilization schemes presented in Table 1. Freeze dried formulations with RTA protein and placebo formulations without protein were created containing 1.0 mg Al/mL, 8 w/v % trehalose and 0.2 or 0 mg/mL rRTA in 10 mM histidine or ammonium acetate buffer pH 6, with either pre-cooling (PC) prior to lyophilization or room temperature incubation prior to lyophilization. Formulations were prepared by mixing with a stir bar at 4-8° C. for 1 hour to allow protein to adsorb to Alhydrogel adjuvant. 1 mL of formulation was placed in a 3 mL glass vial and freeze dried as described in Table 4. Samples from each process condition were incubated at 40° C. and withdrawn for analysis and vaccination studies at 1 week, one month (and continuing through month 6). Pre- and post-lyophilization samples were also obtained.

TABLE 5

Freeze Drying Cycle

| Stage | Time for Step | Initial Temp (° C.) | Final Temp (° C.) | Pressure | Rate |
|---|---|---|---|---|---|
| −10° C. Pre-Cooled Tray Freezing | 0.25 hour | −10 | −10 | Atmospheric | Constant temp −10 |
| | 1 hour | −10 | −40 | Atmospheric | −0.5° C./min |
| | 1 hour | −40 | −40 | Atmospheric | Constant temp −40 |
| Primary Drying | 0.5 hours | −40 | −40 | 60 mTorr | Constant temp −40 |
| | 0.5 hour | −40 | −20 | 60 mTorr | Increase temp |
| | 20 hours | −20 | −20 | 60 mTorr | Constant temp −20 |
| Secondary Drying | 1 hour 40 min | −20 | 0 | 60 mTorr | 0.2° C./min |
| | 1 hour | 0 | 30 | 60 mTorr | 0.5° C./min |
| | 5 hours | 30 | 30 | 60 mTorr | Constant temp 30 |

VII. Particle Size Analysis of Reconstituted Dried Vaccines.

Particle size analysis was done on the solutions before they were freeze dried as well as on the freeze dried samples reconstituted in 1 mL of deionized water. Laser diffraction particle size analysis was conducted using a LS 230 instrument made by Beckman. For the analysis no sonication was done on the sample chamber. The model used for calculating particle size distributions used a solution refractive index of 1.33 and a sample refractive index of 1.57. Approximately 6 mL of sample was required to be added to filtered DI water in the analyzer before the reading was taken. For each run three ninety second averaged particle size distributions were taken. For each formulation three runs were taken. The particle size distribution of the placebo stability study samples is being monitored over with using laser diffraction. The initial Time 0 liquid formulations all had similar particle size distributions and mean particle sizes based on surface area as can be seen in Table 5. When formulations were Tray Freeze Dried from Room Temperature, an increase in particle size was seen. When formulations were Tray Freeze Dried from −10° C. Pre-Cooled Shelves, the particle size distribution stayed very similar to the initial particle size distribution.

TABLE 6

Mean particle size ± standard deviation based on surface area

| | Vaccine | | | |
|---|---|---|---|---|
| Time Point | RT His | RT AA | PC His | PC AA |
| Time 0 - Liquid | 0.35 ± 0.01 | 0.34 ± 0.01 | 0.35 ± 0.01 | 0.35 ± 0.01 |
| Time 0 - FD | 9.43 ± 0.31 | 8.11 ± 0.74 | 0.38 ± 0.06 | 0.49 ± 0.05 |
| Time 1 Week - FD | 10.69 ± 0.41 | 8.96 ± 0.16 | 0.44 ± 0.09 | 0.42 ± 0.05 |
| Time 1 Month - FD | 10.31 ± 0.63 | 9.09 ± 0.12 | 0.46 ± 0.12 | 0.55 ± 0.07 |

VIII. Vaccination of Animals.

Female Swiss Webster mice 5-6 weeks old were vaccinated with 50 μL of the indicated formulations containing 10 microgram of RTA protein subcutaneously on Day 0 and 20. Mice under anesthesia by isoflurane were bled through the retro orbital cavity collecting approximately 2004, of blood on Day 0, 20 and 34. In each group 10 mice were used. Mice were housed 5 per cage and were allowed food and water all the time. Serum was separated from blood by centrifugation at 10,000 rpm for 14 minutes at 4° C.

Figure 15:
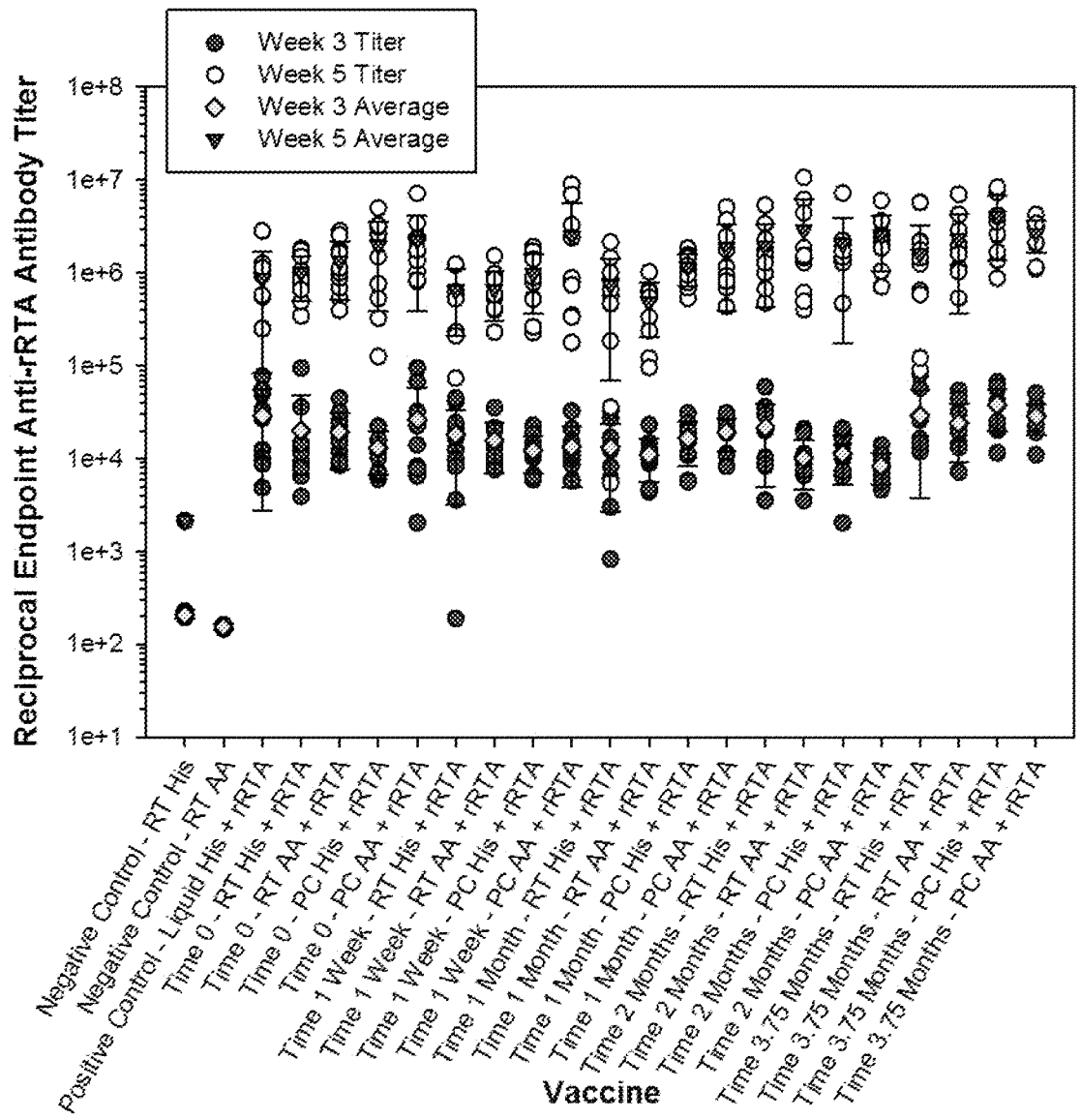
FIG. 15 shows rRTA antibody titers after one injection (week 3) and after two injections (week 5) for each vaccine after no incubation, 1 week and 1 month incubation at 40° C. Average titers are shown as the average of only the mice that responded with the standard deviation of those mice.

Total antibody to RTA in individual sera from vaccinated Swiss Webster mice was determined by ELISA and for determination of neutralizing antibodies (FIGS. 6 and 7). Nunc flat bottom MaxiSorb 96 well plates were coated with 50 μL/well of stock protein diluted in PBS to 1 μg rRTA/mL and incubated at 2-6° C. overnight. Plates were washed 4 times with 300 μL/well of PBS with 0.05% Tween 20. Plates were blocked with 300 μL/well of PBS with 1% BSA and incubated at room temperature for 2 hours. Plates were washed as previously described. 40 μL of PBS with 1% BSA and 0.05% Tween 20 was added to each well. Serum was initially diluted in a dilution buffer of PBS with 1% BSA and 0.05% Tween 20. 70 μL of sample was added to the starting well and then a seven in-plate 2.33-fold dilution was created for each sample. The plate was then incubated for 2 hours at room temperature. Plates were washed again. 40 μL of HRP-conjugated donkey anti-mouse antibody diluted 10,000 times was added to each well and incubated for 2 hours at room temperature. Plates were washed again. TMB was added to each well at 40 μL and incubated for 30 minutes. Stop solution of 2N sulfuric acid was added at 40 μL to each well. The plate was read at 450 nm. Endpoint dilution analysis of individual serum samples from vaccinated mice is shown in FIG. 15. The vaccines tested are abbreviated as follows:

RT His—Negative control (room temperature tray freeze dried in histidine with no protein)

RT AA—Negative control (room temperature tray freeze dried in ammonium acetate with no protein)

His+rRTA Liquid—Positive control (liquid formulation in histidine with protein)

RT His+rRTA—Experimental 1 (room temperature tray freeze dried in histidine with protein)

RT AA+rRTA—Experimental 2 (room temperature tray freeze dried in ammonium acetate with protein)

RPC His+rRTA—Experimental 3 (Pre-Cooled tray freeze dried in histidine with protein)

PC AA+rRTA—Experimental 4 (Pre-Cooled tray freeze dried in ammonium acetate with protein)

When vaccines were stored for one or one month at 40° C., there was no significant difference in the capacity of the vaccines to generate antibodies against RTA (by ELISA) after one injection of 10 microgram (week 3 titers) or 2 injections (week 5) in relationship to vaccine prepared without storage at 40° C. (time 0 in FIG. 15). At week three, 90-100% of mice in each experimental and positive control group responded and by week five all experimental and positive control responded (Table 3). More important, serum obtained from post 2 (week 5) contained antibodies that neutralized ricin (in vitro) where the titers and the proportion of mice with such titers were not obviously different from time 0 vaccines (FIG. 16) or the liquid vaccines (FIG. 17). Further, neutralizing titers decreased after storage of lyophilized RTA vaccine at 40° C. for 1 month, in sera from mice that were given vaccine placed on a room temperature tray before freeze drying. In contrast, vaccines made by precooling prior to freeze drying had better total and neutralizing anti-RTA titers than those immunized with liquid vaccine.

TABLE 7

Number of mice responding to the vaccine after week 3 and week 5

| Vaccine | # of with Antibody Titer | |
|---|---|---|
| | Week 3 | Week 5 |
| Positive Control - Liquid His + rRTA | 9/10 | 10/10 |
| Time 0 - RT His + rRTA | 10/10 | 10/10 |
| Time 0 - RT AA + rRTA | 10/10 | 10/10 |
| Time 0 - PC His + rRTA | 9/10 | 10/10 |
| Time 0 - PC AA + rRTA | 10/10 | 10/10 |
| Time 1 Week - RT His + rRTA | 10/10 | 10/10 |
| Time 1 Week - RT AA + rRTA | 9/9 | 10/10 |
| Time 1 Week - PC His + rRTA | 10/10 | 10/10 |
| Time 1 Week - PC AA + rRTA | 9/10 | 10/10 |
| Time 1 Month - RT His + rRTA | 9/10 | 10/10 |
| Time 1 Month - RT AA + rRTA | 10/10 | 10/10 |
| Time 1 Month - PC His + rRTA | 10/10 | 10/10 |
| Time 1 Month - PC AA + rRTA | 10/10 | 10/10 |

IX. Vaccination of Animals with Vaccines Containing Secondary Co-Adjuvants.

A series of freeze dried formulation was made according to the general lyophilization schemes presented in Table 1. Freeze dried formulations with RTA protein and placebo formulations without protein were created containing 1.0 mg Al/mL, 8 w/v % trehalose and 0.2 or 0 mg/mL rRTA and 60 micrograms of TLR-4 agonist, a synthetic derivative of monophosphoryl Lipid A (MPL) termed PHAD, obtained from Avanti Polar Lipids (Alabaster, Ala.). Vaccines were made in several different manners. In method (1), RTA protein was adsorbed (bound) to aluminum hydroxide in 10 mM histidine or ammonium acetate buffer pH 6 in the presence of 8% trehalose, followed by addition of PHAD agonist to the aqueous suspension. For this method, RTA stored in stabilizer buffer consisting of 10 mM histidine, pH6.0, and 144 mM NaCl, was subjected to dialysis into glycerol- and salt-free buffer prior to adsorption to aluminum adjuvant. In method (2), RTA stored in stabilizing glycerol buffer was diluted 10 fold in 10 mM histidine, pH 6.0, 144 mM NaCl prior to the addition of aluminum to the diluted stabilizing buffer. For this method adsorption was allowed to occur at 4° C. for more than 5 hours so that greater than 95% of the RTA became bound to aluminum gel particles. Subsequently, the aluminum particles were allowed to settle to the bottom of the adsorption vessel or the mixture was subjected to centrifugation to separate the particles from the aqueous buffer. To this Aluminum mixture was added a buffer system (ammonium acetate or histidine) containing 8% trehalose. In this manner the isotonicity of the system could be maintained. For method 1 and method 2, subsequent lyophilization proceeded with either pre-cooling (PC) prior to lyophilization or room temperature incubation prior to lyophilization.

Samples from each process condition were incubated at 4° C. and 40° C. and withdrawn for analysis and vaccination studies at 1 week, one month, 2 months, 3 months, 6 months, 9 months, 12 months, 18 months, and 24 months. For potency analysis, Swiss Webster mice were vaccinated with a concentration range that kept the adjuvant components (aluminum and PHAD) constant while varying the dose of RTA immunogen. For control studies, mice were vaccinated with vaccine that did not contain co-adjuvant PHAD, using the same dose range as the PHAD containing lyophilized vaccines. Two vaccination protocols were used.

One set of mice were vaccinated with one dose of vaccine on study day 1, and another set of mice was vaccinated with vaccine on study days 1 and 21. Serum was obtained from animals at the time of each vaccination and two weeks thereafter. For final analysis, mice were exposed to 10×LD 50 of ricin toxin on day 35 and survivors were recorded. The animals that were vaccinated with the PHAD-containing dried reconstituted vaccine samples demonstrated a significant shift of the dose response curve toward lower doses of RTA immunogen for the serological endpoints (total RTA reactive antibodies and ricin neutralizing antibodies) and also demonstrated protective immunity at the lower dose range when subjected to ricin exposure in comparison to the vaccine without the co-adjuvant. Equally significant, the vaccine samples that were incubated at the higher temperature also demonstrated enhanced immune response, indicating that all of the components of the vaccine were stabilized. Furthermore, the PHAD vaccines induced a broader immune response reflected by a higher titer of neutralizing antibodies and broader response to neutralizing epitopes.

X. Glass Transition Temperature.

Glass transition temperature (Tg) is an indicator of stability of the vaccine product. Below or near the Tg the vaccine behaves as a glass and all components of the vaccines are stabilized within the glass. Above the Tg, the sample becomes is less stable, and the components within the matrix also become less stable. The Tg is measured by differential scanning calorimetry in the following manner. The Tg of the sample is determined by subjecting the sample to a controlled temperature program from 0° C. to 150° C. at a rate of 10° C./min. The heat flow to and from the sample is measured and expressed as a shift in the baseline. The Tg is expressed as the temperature at the midpoint of this baseline shift.

Lyophilized RTA vaccines subjected to DSC analysis demonstrate a high glass transition temperature in excess of 100° C. and lower than 0.5% water content (Karl Fischer analysis).

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A frozen immunogenic composition, comprising:
   (a) an aluminum-salt adjuvant;
   (b) a buffering agent, wherein the buffering agent further comprises a buffering salt and a volatile salt, the volatile salt selected from the group consisting of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate; and
   (c) a glass forming agent wherein the glass-forming agent is selected from the group consisting of trehalose, sucrose, ficoll, dextran, maltotriose, lactose, mannitol and glycine, hydroxyethyl starch, and glycine; and
   (d) at least one protein antigen, wherein the immunogenic composition is frozen.

2. The frozen immunogenic composition of claim 1, wherein the frozen immunogenic composition is further processed by lyophilization to form an essentially dried immunogenic composition.

3. The frozen immunogenic composition of claim 1, wherein the aluminum-salt adjuvant is selected from the group consisting of aluminum hydroxide, aluminum phosphate and aluminum sulfate.

4. The frozen immunogenic composition of claim 1, wherein the aluminum-salt adjuvant is aluminum hydroxide.

5. The frozen immunogenic composition of claim 1, wherein anions of the buffering salt are selected from the group consisting of acetate, succinate, citrate, prolamine, arginine, glycine, histidine, borate, carbonate and phosphate.

6. The frozen immunogenic composition of claim 1, wherein the volatile salt is ammonium acetate or ammonium formate.

7. The frozen immunogenic composition of claim 1, wherein the glass-forming agent is selected from the group consisting of trehalose, sucrose and hydroxyethyl starch.

8. The frozen immunogenic composition of claim 1, wherein the at least one protein antigen is selected from or derived from the group consisting of rotavirus, foot and mouth disease virus, influenza A virus, influenza B virus, influenza C virus, H1N1, H2N2, H3N2, H5N1, H7N7, H1N2, H9N2, H7N2, H7N3, H1ON7, human parainfluenza type 2, herpes simplex virus, Epstein-Barr virus, varicella virus, porcine herpesvirus 1, cytomegalovirus, lyssavirus, Bacillus anthracis, anthrax PA and derivatives, poliovirus, Hepatitis A, Hepatitis B, Hepatitis C, Hepatitis E, distemper virus, Venezuelan equine encephalomyelitis, feline leukemia virus, reovirus, respiratory syncytial virus, Lassa fever virus, polyoma tumor virus, canine parvovirus, papilloma virus, tick borne encephalitis virus, rinderpest virus, human rhinovirus species, Enterovirus species, Mengovirus, paramyxovirus, avian infectious bronchitis virus, human T-cell leukemia-lymphoma virus 1, human immunodeficiency virus-1, human immunodeficiency virus-2, lymphocytic choriomeningitis virus, parvovirus B19, adenovirus, rubella virus, yellow fever virus, dengue virus, bovine respiratory syncitial virus, corona virus, *Bordetella pertussis, Bordetella bronchiseptica, Bordetella parapertussis, Brucella abortis, Brucella melitensis, Brucella suis, Brucella ovis, Brucella* species, *Escherichia coli, Salmonella* species, *Salmonella typhi*, Streptococci, *Vibrio cholera, Vibrio parahaemolyticus, Shigella, Pseudomonas*, tuberculosis, avium, Bacille Calmette Guerin, *Mycobacterium leprae*, Pneumococci, Staphlylococci, *Enterobacter* species, *Rochalimaia henselae, Pasteurella haemolytica, Pasteurella multocida, Chlamydia trachomatis, Chlamydia psittaci, Lymphogranuloma venereum, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia rickettsii, Rickettsia typhi, Rickettsia prowsaekii, Ehrlichia chaffeensis, Anaplasma phagocytophilum, Plasmodium falciparum, Plasmodium vivax, Plasmodium malariae, Schistosomes*, trypanosomes, *Leishmania* species, *Filarial nematodes*, trichomoniasis, sarcosporidiasis, *Taenia saginata, Taenia solium, Leishmania, Toxoplasma gondii, Trichinella spiralis*, coccidiosis, *Eimeria tenella, Cryptococcus neoformans, Candida albican, Apergillus fumigatus*, coccidioidomycosis, *Neisseria gonorrhoeae*, malaria circumsporozoite protein, malaria merozoite protein, trypanosome surface antigen protein, pertussis, alphaviruses, adenovirus, diphtheria toxoid, tetanus toxoid, meningococcal outer membrane protein, streptococcal M protein, Influenza hemagglutinin, cancer antigen, tumor antigens, toxins, *Clostridium perfringens* epsilon toxin, ricin toxin, *Pseudomonas* exotoxin, exotoxins, neurotoxins, cytokines, cytokine receptors, monokines, monokine receptors, plant pollens, animal dander, and dust mites.

9. The frozen immunogenic composition of claim 2, wherein the essentially dry immunogenic composition is reconstituted and the adjuvant particles in the reconstituted immunogenic composition have reduced aggregation and agglomeration when compared to a composition without a volatile salt.

10. The frozen immunogenic composition of claim 1, wherein the protein antigen is a protein agent derived from a virus.

11. The frozen immunogenic composition of claim 2, wherein the essentially dried immunogenic compositions is reconstituted in a pharmaceutically acceptable diluent.

12. A kit comprising the immunogenic composition according to claim 1, and a container.

13. The frozen immunogenic composition of claim 1, wherein the volatile salt is ammonium acetate or ammonium formate and the glass-forming agent is selected from the group consisting of trehalose, sucrose and hydroxyethyl starch.

* * * * *